(12) United States Patent  (10) Patent No.: US 8,709,424 B2
Schebye et al.  (45) Date of Patent: Apr. 29, 2014

(54) ANTI-GITR ANTIBODIES

(75) Inventors: Xiao Min Schebye, San Carlos, CA (US); Grigori P. Ermakov, Santa Clara, CA (US); Douglas J. Hodges, Sunnyvale, CA (US); Leonard G. Presta, San Francisco, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/388,270

(22) PCT Filed: Aug. 31, 2010

(86) PCT No.: PCT/US2010/047248
§ 371 (c)(1),
(2), (4) Date: Apr. 10, 2012

(87) PCT Pub. No.: WO2011/028683
PCT Pub. Date: Mar. 10, 2011

(65) Prior Publication Data
US 2012/0189639 A1  Jul. 26, 2012

Related U.S. Application Data

(60) Provisional application No. 61/239,667, filed on Sep. 3, 2009, provisional application No. 61/307,767, filed on Feb. 24, 2010, provisional application No. 61/313,955, filed on Mar. 15, 2010.

(51) Int. Cl.
| | | |
|---|---|---|
| *A61K 39/395* | (2006.01) | |
| *C12P 21/08* | (2006.01) | |
| *C07H 21/04* | (2006.01) | |
| *C07K 16/00* | (2006.01) | |

(52) U.S. Cl.
USPC ............... 424/143.1; 424/158.1; 424/172.1; 530/387.3; 530/388.22

(58) Field of Classification Search
None
See application file for complete search history.

(56) References Cited

U.S. PATENT DOCUMENTS

| | | |
|---|---|---|
| 7,812,135 B2 | 10/2010 | Smith et al. |
| 2002/0010320 A1 | 1/2002 | Fett et al. |
| 2002/0103345 A1 | 8/2002 | Zhu |
| 2002/0141989 A1 | 10/2002 | Kricek et al. |
| 2002/0150993 A1* | 10/2002 | Ashkenazi et al. .......... 435/69.5 |
| 2002/0164339 A1 | 11/2002 | do Couto et al. |
| 2003/0045691 A1 | 3/2003 | Ono et al. |
| 2003/0099655 A1 | 5/2003 | Watkins et al. |
| 2003/0133932 A1 | 7/2003 | Zhou et al. |
| 2003/0190598 A1 | 10/2003 | Tanha et al. |
| 2004/0052783 A1 | 3/2004 | Weiner et al. |
| 2004/0110930 A1 | 6/2004 | Reinl et al. |
| 2004/0137513 A1 | 7/2004 | Oevaux et al. |
| 2004/0157214 A1 | 8/2004 | McCafferty et al. |
| 2004/0175379 A1 | 9/2004 | DeVries et al. |
| 2005/0048050 A1 | 3/2005 | Fujita-Yamaguchi |
| 2005/0118183 A1 | 6/2005 | Hoffee et al. |
| 2005/0153872 A1 | 7/2005 | Qiu |
| 2005/0154192 A1 | 7/2005 | Shirakawa et al. |
| 2005/0265998 A1 | 12/2005 | Elson |
| 2005/0266003 A1 | 12/2005 | Lin et al. |
| 2006/0018909 A1 | 1/2006 | Oliner et al. |
| 2006/0140932 A1 | 6/2006 | Dickinson et al. |
| 2006/0165695 A1 | 7/2006 | Shitara et al. |
| 2006/0167230 A1 | 7/2006 | Koga et al. |
| 2006/0233788 A1 | 10/2006 | Heiman et al. |
| 2006/0263369 A1 | 11/2006 | Bicknell et al. |
| 2007/0009901 A1 | 1/2007 | Doucette-Stamm et al. |
| 2007/0041978 A1 | 2/2007 | Hattori et al. |
| 2007/0098719 A1 | 5/2007 | Smith et al. |
| 2008/0025913 A1 | 1/2008 | Bowdish et al. |
| 2008/0138336 A1 | 6/2008 | Damschroder et al. |
| 2008/0166756 A1 | 7/2008 | Tsuchiya et al. |
| 2008/0175835 A1 | 7/2008 | Acton et al. |
| 2008/0175856 A1 | 7/2008 | Meinke et al. |
| 2008/0206239 A1 | 8/2008 | Jones et al. |
| 2008/0241069 A1 | 10/2008 | Paterson |
| 2008/0286290 A1 | 11/2008 | Furusako et al. |
| 2008/0292620 A1 | 11/2008 | Damiano et al. |
| 2009/0028851 A1 | 1/2009 | Stuhmer et al. |
| 2009/0041783 A1 | 2/2009 | Takayama et al. |
| 2009/0092609 A1 | 4/2009 | Crowe, Jr. |
| 2009/0110682 A1 | 4/2009 | Yanagisawa et al. |
| 2009/0110685 A1 | 4/2009 | Patel et al. |
| 2009/0137782 A1 | 5/2009 | Old et al. |
| 2009/0197330 A1 | 8/2009 | Numazaki et al. |
| 2009/0215092 A1 | 8/2009 | Love et al. |

FOREIGN PATENT DOCUMENTS

| | | |
|---|---|---|
| WO | WO 2006105021 A2 * | 10/2006 |
| WO | WO 2009/009116 | 1/2009 |

OTHER PUBLICATIONS

Bowie et al. Deciphering the message in protein sequences:tolerance to amino acid substitutions. Science, 247:1306-1310, 1990.*
Strohl. Optimization of Fc-mediated effector functions of monoclonal antibodies. Current Opinion in Biotechnology. 20:685-691, Nov. 2009.*
Presta. Molecular engineering and design of therapeutic antibodies. Current Opinion in Immunology. 20(4):460-470. Aug. 2008.*
Cohen et al. (2006) *Cancer Res*. 66(9):4904-12 "Agonist anti-GITR antibody enhances vaccine-induced CD8(+) T-cell responses and tumor immunity".
Ko et al., (2005) *J Exp Med*. 202(7):885-91. Epub Sep. 26, 2005 "Treatment of advanced tumors with agonistic anti-GITR mAb and its effects on tumor-infiltrating Foxp3+CD25+CD4+ regulatory T cells".
Nocentini et al. (2007) *Ann N Y Acad Sci*. 1107:380-91 "Modulation of acute and chronic inflammation of the lung by GITR and its ligand".

(Continued)

*Primary Examiner* — Vanessa L Ford
*Assistant Examiner* — Sandra Dillahunt
(74) *Attorney, Agent, or Firm* — Sheela Mohan-Peterson

(57) ABSTRACT

Antibodies to human GITR are provided, as well as uses thereof, e.g., in treatment of proliferative and immune disorders.

6 Claims, 2 Drawing Sheets

(56) References Cited

OTHER PUBLICATIONS

Ramirez-Montagut et al. (2006) *J Immunol.* 176(11):6434-42 "Glucocorticoid-induced TNF receptor family related gene activation overcomes tolerance/ignorance to melanoma differentiation antigens and enhances antitumor immunity".

Zhou et al. (2007) *J Immunol.* 179(11):7365-75 "Pivotal roles of CD4+ effector T cells in mediating agonistic anti-GITR mAb-induced-immune activation and tumor immunity in CT26 tumors".

Cuzzocrea, et al. (2004) *J. Leukoc. Biol.* 76(5):933-940 "Glucocorticoid-induced TNF receptor family gene (GITR) knock-out mice exhibit a resistance to splanchnic artery occlusion (SAO) shock".

Cuzzocrea, et al. (2006) *J. Immunol.* 177(1):631-641 "Proinflammatory role of glucocorticoid-induced TNF receptor-related gene in acute lung inflammation".

Cuzzocrea et al. (2007) *FASEB J.* 21(1):117-129 "Genetic and pharmacological inhibition of GITR-GITRL interaction reduces chronic lung injury induced by bleomycin instillation".

Hanabuchi et al. (2006) *Blood* 107(9):3617-3623 "Human plasmacytoid predendritic cells activate NK cells through glucocorticoid-induced tumor necrosis factor receptor-ligand (GITRL)".

McHugh, et al. (2002) *Immunity* 16(2):311-323 "CD4(+)CD25(+) immunoregulatory T cells: gene expression analysis reveals a functional role for the glucocorticoid-induced TNF receptor".

Nocentini and Riccardi (2005) *Eur. J. Immunol.* 2005. 35(4):1016-1022 "GITR: a multifaceted regulator of immunity belonging to the tumor necrosis factor receptor superfamily".

Ronchetti, et al. (2004) *Eur. J. Immunol.* 34(3):613-622 "GITR, a member of the TNF receptor superfamily, is costimulatory to mouse T lymphocyte subpopulations".

Shevach and Stephens (2006) *Nat. Rev. Immunol.* 6(8):613-618 "The GITR-GITRL interaction: co-stimulation or contrasuppression of regulatory activity?".

Shimizu, et al. (2002) *Nat. Immunol..* 3(2):135-142 "Stimulation of CD25(+)CD4(+) regulatory T cells through GITR breaks immunological self-tolerance".

Shin, et al. (2002) *Cytokine* 19(4):187-192 "Recombinant glucocorticoid induced tumour necrosis factor receptor (rGITR) induced COX-2 activity in murine macrophage Raw 264.7 cells".

Suvas, et al. (2005) *J. Virol.* 79(18):11935-11942 "In vivo kinetics of GITR and GITR ligand expression and their functional significance in regulating viral immunopathology".

Tone, et al. (2003) *Proc. Natl. Acad. Sci. USA* 100(25):15059-15064 "Mouse glucocorticoid-induced tumor necrosis factor receptor ligand is costimulatory for T cells".

\* cited by examiner

```
1         9              24 25                     47
QRPTGGPG  CGPGRLLLGTGTDARC  CRVHTTRCCRDYPGEECCSEWDC  M
          |---Module 1----|  |-------Module 2-------|

49             64      69              87
CVQPEFHCGDPCCTTC  RHHP  CPPGQGVQSQGKFSFGFQC  ID

|---Module 3----|       |-----Module 4-----|

90         103      109              128
CASGTFSGGHEGHC  KPWTD  CTQFGFLTVFPGNKTHNAVC

|--Module 5---|        |-----Module 6------|

VPGSPPAEPLGWLTVVLLAVAACVLLLTSAQLGLHIWQLRSQCMWPRETQLLLEVPPSTEDA
                          216
RSCQFPEEERGERSAEEKGRLGDLWV   (SEQ ID NO: 89)
```

ANTI-GITR ANTIBODIES

The Sequence Listing filed electronically herewith is also hereby incorporated by reference in its entirety (File Name: "BP2009_6860-US-PCT_SeqListing"; Date Created: Jan. 31, 2012; File Size: 64.4 KB.)

FIELD OF THE INVENTION

The present invention relates generally to antibodies specific for Glucocorticoid-induced TNF receptor (GITR) and uses thereof. More specifically, the invention relates to humanized antibodies that recognize human GITR and modulate its activity, particularly in immune and proliferative disorders.

BACKGROUND OF THE INVENTION

Glucocorticoid-induced TNFR-related protein (GITR), a member of the TNFR superfamily, is expressed in many components of the innate and adaptive immune system (see, e.g., Hanabuchi et al. (2006) *Blood* 107:3617-3623; and Nocentini and Riccardi (2005) *Eur. J. Immunol.* 2005. 35:1016-1022). Its membrane expression is increased following T cell activation (Hanabuchi, supra; and Nocentini and Riccardi, supra); its triggering co-activates effector T lymphocytes and modulates regulatory T cell (Treg) activity (see, e.g., McHugh, et al. (2002) *Immunity* 2002. 16:311-323; Shimizu, et al. (2002) *Nat. Immunol.* 3:135-142; Ronchetti, et al (2004) *Eur. J. Immunol.* 34:613-622; and Tone, et al. (2003) *Proc. Natl. Acad. Sci. USA* 100:15059-15064.

GITR is activated by GITR ligand (GITRL), which is mainly expressed on APC and has been suggested to deliver signals by its cytoplasmic domain, although further studies are necessary to define the biochemical signaling (Nocentini, supra; Ronchetti, supra; Suvas, et al. (2005) *J. Virol.* 79:11935-11942; and Shin, et al. (2002) *Cytokine* 19:187-192).

GITR activation increases resistance to tumors and viral infections, is involved in autoimmune/inflammatory processes and regulates leukocyte extravasation (Nocentini supra; Cuzzocrea, et al. (2004) *J. Leukoc. Biol.* 76:933-940; Shevach et al. (2006) *Nat. Rev. Immunol.* 6:613-618; Cuzzocrea, et al. (2006) *J. Immunol.* 177:631-641; and Cuzzocrea et al. (2007) *FASEB J.* 21:117-129).

The need exists for improved methods and compositions for the treatment of immune and proliferative disorders, e.g., tumors and cancers, by use of agents that modulate GITR activity. Preferably, such agonists would have a high affinity for the target molecule, and would be able to stimulate GITR signaling at relatively low doses. Preferably, such methods and compositions would be highly specific for GITR, and not interfere with the activity of other receptors. Preferably, such methods and compositions would employ agonists suitable for modification for the delivery of cytotoxic payloads to target cells, but also suitable for non-cytotoxic uses. Preferably, such methods and compositions would employ antibodies modified to limit their antigenicity when administered to a subject in need thereof.

BRIEF DESCRIPTION OF THE DRAWING

FIG. 2 shows the modules of GITR as determined by the method described in Naismith and Sprang (1998) *Trends Biochem. Sci.* 23:74-79. Bold residues indicate the conformational DTA-1-like epitope as determined below.

SUMMARY OF THE INVENTION

Figure 1:
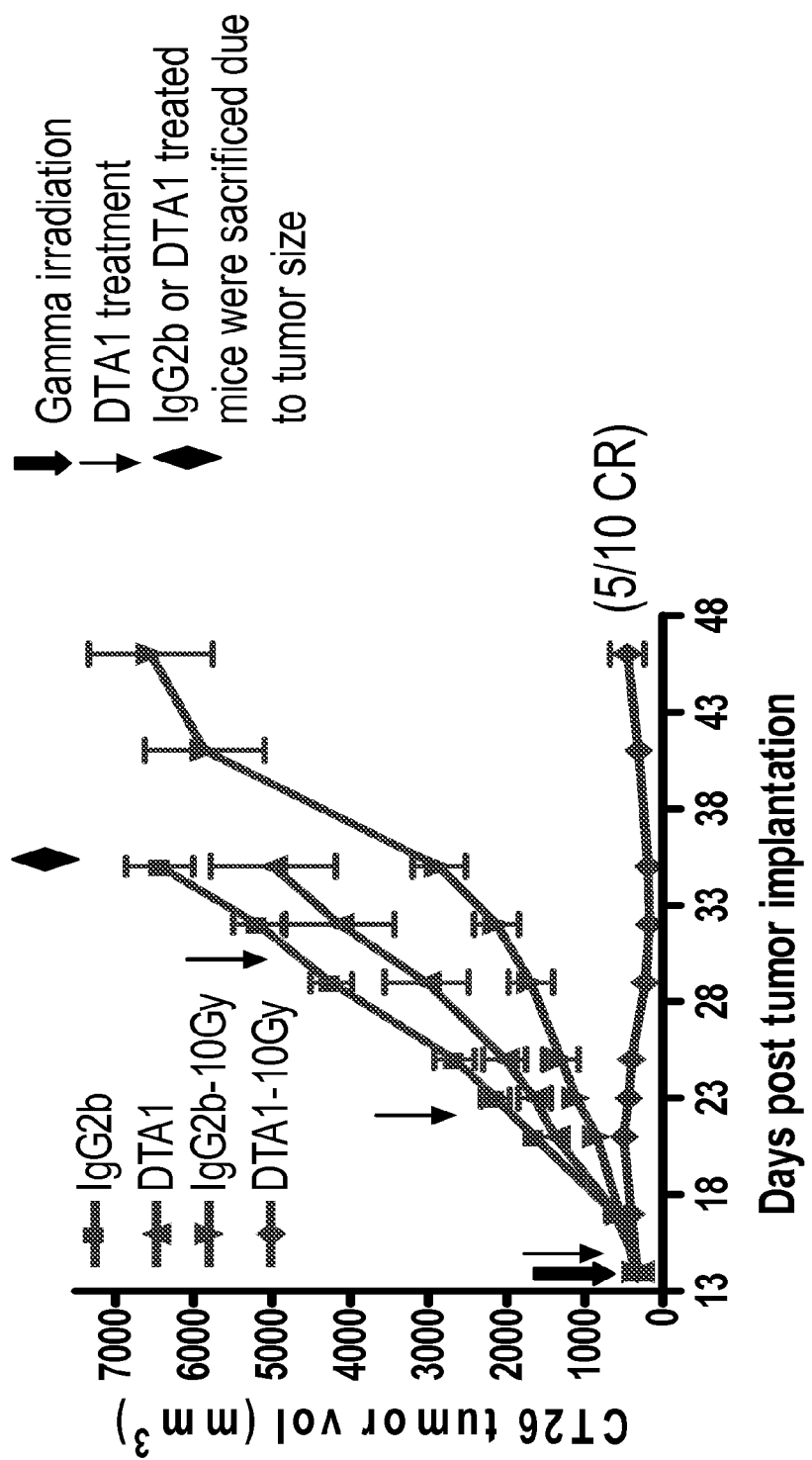
FIG. 1 shows the synergistic effect of combined treatment with DTA-1 (specific for mGITR; see, e.g., Shimizu, et al. (2002) *Nature Immunol.* 3:135-142) and local irradiation. "CR" means complete regression.

The present invention meets these needs in the art and more by providing agonists of GITR, e.g. humanized anti-GITR antibodies.

In one aspect the invention provides binding compounds, such as an antibodies or fragment thereof, including humanized or chimeric recombinant antibodies, that binds human GITR, comprising an antibody light chain variable domain, or antigen binding fragment thereof, having at least one or more CDRs selected from the group consisting of SEQ ID NOs: 56-88 and a heavy chain variable domain, having at least one or more CDRs selected from the group consisting of SEQ ID NOs: 23-55.

In other embodiments the binding compound of the present invention comprises a light chain variable domain and a heavy chain variable domain, or the antigen binding fragments thereof, described in the preceding two paragraphs.

In some embodiments, the binding compound comprises a framework region, wherein the amino acid sequence of the framework region is all or substantially all of a human immunoglobulin amino acid sequence.

In some embodiments the light chain variable domain comprises a sequence selected from the group consisting of SEQ ID NOs: 12-22 or a variant thereof. In some embodiments the heavy chain variable domain comprises a sequence selected from the group consisting of SEQ ID NOs: 1-11. In yet a further embodiment, the binding compound comprises a light chain variable domain and a heavy chain variable domain, or the antigen binding fragments thereof, described in this paragraph.

In other embodiments the binding compound of the present invention comprises a light chain variable domain, or an antigen binding fragment thereof, consisting essentially of a sequence selected from the group consisting of SEQ ID NOs: 91, 93, 95, 97, 99, 101, 103, 105, 107, 109, 111, and/or a heavy chain variable domain, or an antigen binding fragment thereof, consisting essentially of a sequence selected from the group consisting of SEQ ID NOs: 90, 92, 94, 96, 98, 100, 102, 104, 106, 108, 110.

In one embodiment, the invention relates to antibodies that are able to block the binding of a binding compound of the present invention to human GITR in a cross-blocking assay. In various embodiments the antibody is able to block binding of human GITR to an antibody comprising the CDR sequences of antibodies 36E5, 3D6, 61G6, 6H6, 61F6, 1D8, 17F10, 35D8, 49A1, 9E5, or 31H6 as disclosed herein. In another embodiment, the invention relates to binding compounds that are able to block GITR-mediated activity, such activities including but not limited to, co-stimulation of naïve CD4+ T cell proliferation assay.

In some embodiments, the binding compound of the present invention further comprises a heavy chain constant region, wherein the heavy chain constant region comprises a γ1, γ2, γ3, or γ4 human heavy chain constant region or a variant thereof. In various embodiments the light chain constant region comprises a lambda or a kappa human light chain constant region.

In various embodiments the binding compounds of the present invention are polyclonal, monoclonal, chimeric, humanized or fully human antibodies or fragments thereof.

The present invention also contemplates that the antigen binding fragment is an antibody fragment selected from the group consisting of Fab, Fab', Fab'-SH, Fv, scFv, F(ab')$_2$, and a diabody.

The present invention encompasses a method of enhancing an immune response in a human subject comprising administering to a subject in need thereof an antibody (or a antigen binding fragment thereof) specific for GITR in an amount effective to stimulate GITR signaling. In some embodiments, the antibody specific for GITR is the humanized or chimeric antibody. In further embodiments, the immune response is an anti-infective or anti-viral response. In certain embodiments, the GITR antibody or antigen binding fragment thereof is co-administered with a TGFβ antibody or local radiation.

The present invention encompasses an isolated nucleic acid encoding the polypeptide sequence of an antibody embodiment of the binding compound of the present invention. The nucleic acid can be in an expression vector operably linked to control sequences recognized by a host cell transfected with the vector. Also encompassed is a host cell comprising the vector, and a method of producing a polypeptide comprising culturing the host cell under conditions wherein the nucleic acid sequence is expressed, thereby producing the polypeptide, and recovering the polypeptide from the host cell or medium.

The present invention provides an antibody or antigen binding fragment thereof, produced by a hybridoma deposited at the American Type Culture Collection (ATCC), wherein the hybridoma is selected from the group consisting of PTA-9889, PTA-9890, PTA-9891, PTA-9892, PTA-9893, PTA-10286, PTA-10287, PTA-10288, PTA-10289, PTA-10290, and PTA-10291.

The present invention encompasses an antibody or antigen binding fragment that binds to human GITR protein, wherein the antibody or antigen binging fragment recognizes an epitope spanning module 3 and module 4 of human GITR protein (SEQ ID NO: 89). In certain embodiments, the epitope comprises $Gly^{57}$, $Arg^{65}$, $His^{67}$, $Lys^{80}$, $Phe^{81}$, $Ser^{82}$, and $Gln^{86}$. In yet other embodiments the antibody cross-blocks at least one of the antibodies or antibody fragments produced by the hybridomas selected from group consisting of PTA-9889, PTA-9890, PTA-9891, PTA-9892, PTA-9893, PTA-10286, PTA-10287, PTA-10288, PTA-10289, PTA-10290, and PTA-10291.

DETAILED DESCRIPTION

As used herein, including the appended claims, the singular forms of words such as "a," "an," and "the," include their corresponding plural references unless the context clearly dictates otherwise. Table 15 below provides a listing of sequence identifiers used in this application. All references cited herein are incorporated by reference to the same extent as if each individual publication, database entry (e.g. Genbank sequences or GeneID entries), patent application, or patent, was specifically and individually indicated to be incorporated by reference. Citation of the references herein is not intended as an admission that any of the foregoing is pertinent prior art, nor does it constitute any admission as to the contents or date of these publications or documents.

I. Definitions

The terms "GITR", "Glucocorticoid-induced TNFR-related protein", "Activation-inducible TNFR family receptor", "AITR", "Tumor necrosis factor receptor superfamily member 18", and "TNFSF18" are well known in the art. The human and mouse GITR nucleotide and polypeptide sequences are disclosed in WO 98/06842. GenBank® deposits of the human GITR amino sequence (Q9Y5U5) and mouse GITR nucleic and amino acid sequences (AF109216) are also available.

"Proliferative activity" encompasses an activity that promotes, that is necessary for, or that is specifically associated with, e.g., normal cell division, as well as cancer, tumors, dysplasia, cell transformation, metastasis, and angiogenesis.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. "Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of an agent with animal subject, a cell, tissue, physiological compartment, or physiological fluid. "Treatment of a cell" also encompasses situations where the agent contacts GITR, e.g., in the fluid phase or colloidal phase, but also situations where the agonist or antagonist does not contact the cell or the receptor.

As used herein, the term "antibody" refers to any form of antibody that exhibits the desired biological activity. Thus, it is used in the broadest sense and specifically covers monoclonal antibodies (including full length monoclonal antibodies), polyclonal antibodies, multispecific antibodies (e.g., bispecific antibodies), chimeric antibodies, humanized antibodies, fully human antibodies, etc. so long as they exhibit the desired biological activity.

As used herein, the terms "GITR binding fragment," "binding fragment thereof" or "antigen binding fragment thereof" encompass a fragment or a derivative of an antibody that still substantially retains its biological activity of inducing GITR signaling referred to herein as "GITR inducing activity." The term "antibody fragment" or GITR binding fragment refers to a portion of a full length antibody, generally the antigen binding or variable region thereof. Examples of antibody fragments include Fab, Fab', F(ab')$_2$, and Fv fragments; diabodies; linear antibodies; single-chain antibody molecules, e.g., sc-Fv; and multispecific antibodies formed from antibody fragments. Typically, a binding fragment or derivative retains at least 10% of its GITR agonist activity. Preferably, a binding fragment or derivative retains at least 25%, 50%, 60%, 70%, 80%, 90%, 95%, 99% or 100% (or more) of its GITR agonist activity, although any binding fragment with sufficient affinity to exert the desired biological effect will be useful. It is also intended that a GITR binding fragment can include variants having conservative amino acid substitutions that do not substantially alter its biologic activity.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. U.S. Pat. No. 4,816,567; Morrison et al. (1984) *Proc. Natl. Acad. Sci. USA* 81: 6851-6855.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

As used herein, the term "single-chain Fv" or "scFv" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun (1994) THE PHARMACOLOGY OF MONOCLONAL ANTIBODIES, vol. 113, Rosenburg and Moore eds. Springer-Verlag, New York, pp. 269-315.

The monoclonal antibodies herein also include camelized single domain antibodies. See, e.g., Muyldermans et al. (2001) *Trends Biochem. Sci.* 26:230; Reichmann et al. (1999) *J. Immunol. Methods* 231:25; WO 94/04678; WO 94/25591; U.S. Pat. No. 6,005,079). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

As used herein, the term "humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

The antibodies of the present invention also include antibodies with modified (or blocked) Fc regions to provide altered effector functions. See, e.g., U.S. Pat. No. 5,624,821; WO2003/086310; WO2005/120571; WO2006/0057702; Presta (2006) *Adv. Drug Delivery Rev.* 58:640-656. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, and a longer half-life would result in less frequent dosing, with the concomitant increased convenience and decreased use of material. See Presta (2005) *J. Allergy Clin. Immunol.* 116:731 at 734-35.

The antibodies of the present invention also include antibodies with intact Fc regions that provide full effector functions, e.g. antibodies of isotype IgG1, which induce complement-dependent cytotoxicity (CDC) or antibody dependent cellular cytotoxicity (ADCC) in a targeted cell.

The antibodies of the present invention also include antibodies conjugated to cytotoxic payloads, such as cytotoxic agents or radionuclides. Such antibody conjugates may be used in immunotherapy in conjunction with anti-GITR treatment, to selectively target and kill cells expressing certain antigens on their surface. Exemplary cytotoxic agents include ricin, vinca alkaloid, methotrexate, Psuedomonas exotoxin, saporin, diphtheria toxin, cisplatin, doxorubicin, abrin toxin, gelonin and pokeweed antiviral protein. Exemplary radionuclides for use in immunotherapy with the antibodies of the present invention include $^{125}$I, $^{131}$I, $^{90}$Y, $^{67}$Cu, $^{211}$At, $^{171}$Lu, $^{143}$Pr and $^{213}$Bi. e.g., U.S. Patent Application Publication No. 2006/0014225.

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences, respectively. A fully human antibody may be generated in a human being, in a transgenic animal having human immunoglobulin germline sequences, by phage display or other molecular biological methods.

As used herein, the term "hypervariable region" refers to the amino acid residues of an antibody that are responsible for antigen-binding. The hypervariable region comprises amino acid residues from a "complementarity determining region" or "CDR" (e.g. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain (Kabat et al. (1991) Sequences of Proteins of Immunological Interest, 5th Ed. Public Health Service, National Institutes of Health, Bethesda, Md.) and/or those residues from a "hypervariable loop" (e.g., residues 26-32 (L1), 50-52 (L2) and 91-96 (L3) in the light chain variable domain and 26-32 (H1), 53-55 (H2) and 96-101 (H3) in the heavy chain variable domain (Chothia and Lesk (1987) J. Mol. Biol. 196: 901-917). As used herein, the term "framework" or "FR" residues refers to those variable domain residues other than the hypervariable region residues defined herein as CDR residues. The residue numbering above relates to the Kabat numbering system and does not necessarily correspond in detail to the sequence numbering in the accompanying Sequence Listing.

"Binding compound" refers to a molecule, small molecule, macromolecule, polypeptide, antibody or fragment or analogue thereof, or soluble receptor, capable of binding to a target. "Binding compound" also may refer to a complex of molecules, e.g., a non-covalent complex, to an ionized molecule, and to a covalently or non-covalently modified molecule, e.g., modified by phosphorylation, acylation, cross-linking, cyclization, or limited cleavage, that is capable of binding to a target. When used with reference to antibodies, the term "binding compound" refers to both antibodies and antigen binding fragments thereof. "Binding" refers to an association of the binding composition with a target where the association results in reduction in the normal Brownian motion of the binding composition, in cases where the binding composition can be dissolved or suspended in solution. "Binding composition" refers to a molecule, e.g. a binding compound, in combination with a stabilizer, excipient, salt, buffer, solvent, or additive, capable of binding to a target.

"Conservatively modified variants" or "conservative substitution" refers to substitutions of amino acids are known to those of skill in this art and may often be made even in essential regions of the polypeptide without altering the biological activity of the resulting molecule. Such exemplary substitutions are preferably made in accordance with those set forth in Table 1 as follows:

TABLE 1

| Exemplary Conservative Amino Acid Substitutions | |
|---|---|
| Original residue | Conservative substitution |
| Ala (A) | Gly; Ser |
| Arg (R) | Lys, His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |

TABLE 1-continued

| Exemplary Conservative Amino Acid Substitutions | |
|---|---|
| Original residue | Conservative substitution |
| Trp (W) | Tyr; Phe |
| Tyr (Y) | Trp; Phe |
| Val (V) | Ile; Leu |

Those of skill in this art recognize that, in general, single amino acid substitutions in non-essential regions of a polypeptide may not substantially alter biological activity. See, e.g., Watson et al. (1987) Molecular Biology of the Gene, The Benjamin/Cummings Pub. Co., p. 224 (4th Edition).

The phrase "consists essentially of," or variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, a binding compound that consists essentially of a recited amino acid sequence may also include one or more amino acids, including substitutions of one or more amino acid residues, that do not materially affect the properties of the binding compound.

"Effective amount" encompasses an amount sufficient to ameliorate or prevent a symptom or sign of the medical condition. Effective amount also means an amount sufficient to allow or facilitate diagnosis. An effective amount for a particular patient or veterinary subject may vary depending on factors such as the condition being treated, the overall health of the patient, the method route and dose of administration and the severity of side affects. See, e.g., U.S. Pat. No. 5,888, 530. An effective amount can be the maximal dose or dosing protocol that avoids significant side effects or toxic effects. The effect will result in an improvement of a diagnostic measure or parameter by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject. See, e.g., Maynard et al. (1996) A Handbook of SOPs for Good Clinical Practice, Interpharm Press, Boca Raton, Fla.; Dent (2001) Good Laboratory and Good Clinical Practice, Urch Publ., London, UK.

"Immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis, including infections, tumors, and cancers that resist eradication by the immune system. "Cancerous condition" includes, e.g., cancer, cancer cells, tumors, angiogenesis, and precancerous conditions such as dysplasia.

The term immune disorder means a disease in which a component of the immune system of a mammal causes, mediates or otherwise contributes to a morbidity in the mammal. Also included are diseases in which stimulation or intervention of the immune response has an ameliorative effect on progression of the disease. Included within this term are autoimmune diseases, immune-mediated inflammatory diseases, non-immune-mediated inflammatory diseases, infectious diseases, and immunodeficiency diseases. Examples of immune-related and inflammatory diseases, some of which are immune or T cell mediated, which can be treated according to the invention include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory and fibrotic lung diseases such as inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease. Infectious diseases include AIDS (HIV infection), hepatitis A, B, C, D, and E, bacterial infections, fungal infections, protozoal infections and parasitic infections.

The terms "cancer", "tumor", "cancerous", and "malignant" refer to or describe the physiological condition in mammals that is typically characterized by unregulated cell growth. Examples of cancer include but are not limited to, carcinoma including adenocarcinoma, lymphoma, blastoma, melanoma, sarcoma, and leukemia. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, glioma, cervical cancer, ovarian cancer, liver cancer such as hepatic carcinoma and hepatoma, bladder cancer, breast cancer, colon cancer, colorectal cancer, endometrial carcinoma, myeloma (such as multiple myeloma), salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer.

As cancerous cells grow and multiply, they form a mass of cancerous tissue, that is a tumor, which invades and destroys normal adjacent tissues. Malignant tumors are cancer. Malignant tumors usually can be removed, but they may grow back. Cells from malignant tumors can invade and damage nearby tissues and organs. Also, cancer cells can break away from a malignant tumor and enter the bloodstream or lymphatic system, which is the way cancer cells spread from the primary tumor (i.e., the original cancer) to form new tumors in other organs. The spread of cancer in the body is called metastasis (What You Need to Know About Cancer—an Overview, NIH Publication No. 00-1566; posted Sep. 26, 2000, updated Sep. 16, 2002 (2002)).

As used herein, the term "solid tumor" refers to an abnormal growth or mass of tissue that usually does not contain cysts or liquid areas. Solid tumors may be benign (not cancerous) or malignant (cancerous). Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

As used herein, the term "primary cancer" refers to the original tumor or the first tumor. Cancer may begin in any organ or tissue of the body. It is usually named for the part of the body or the type of cell in which it originates (Metastatic Cancer: Questions and Answers, Cancer Facts 6.20, National Cancer Institute, reviewed Sep. 1, 2004 (2004)).

As used herein, the term "carcinoma in situ" refers to cancerous cells that are still contained within the tissue where they started to grow, and have not yet become invasive or spread to other parts of the body.

As used herein, the term "carcinomas" refers to cancers of epithelial cells, which are cells that cover the surface of the body, produce hormones, and make up glands. Examples of carcinomas are cancers of the skin, lung, colon, stomach, breast, prostate and thyroid gland.

As used herein, the term "isolated nucleic acid molecule" refers to a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences involved in the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, "polymerase chain reaction" or "PCR" refers to a procedure or technique in which minute amounts of a specific piece of nucleic acid, RNA and/or DNA, are amplified as described in, e.g., U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) *Cold Spring Harbor Symp. Quant. Biol.* 51:263; Erlich, ed., (1989) PCR TECHNOLOGY (Stockton Press, N.Y.) As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

As used herein, the term "germline sequence" refers to a sequence of unrearranged immunoglobulin DNA sequences, including rodent (e.g. mouse) and human germline sequences. Any suitable source of unrearranged immunoglobulin DNA may be used. Human germline sequences may be obtained, for example, from JOINSOLVER® germline databases on the website for the National Institute of Arthritis and Musculoskeletal and Skin Diseases of the United States National Institutes of Health. Mouse germline sequences may be obtained, for example, as described in Giudicelli et al. (2005) *Nucleic Acids Res.* 33:D256-D261.

To examine the extent of enhancement of GITR activity, for example, samples or assays comprising a given, e.g., protein, gene, cell, or organism, are treated with a potential activating or inhibiting agent and are compared to control samples without the agent. Control samples, i.e., not treated with agent, are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 20%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Endpoints in activation or inhibition can be monitored as follows. Activation, inhibition, and response to treatment, e.g., of a cell, physiological fluid, tissue, organ, and animal or human subject, can be monitored by an endpoint. The endpoint may comprise a predetermined quantity or percentage of, e.g., an indicia of inflammation, oncogenicity, or cell degranulation or secretion, such as the release of a cytokine, toxic oxygen, or a protease. The endpoint may comprise, e.g., a predetermined quantity of ion flux or transport; cell migration; cell adhesion; cell proliferation; potential for metastasis; cell differentiation; and change in phenotype, e.g., change in expression of gene relating to inflammation, apoptosis, transformation, cell cycle, or metastasis (see, e.g., Knight (2000) *Ann. Clin. Lab. Sci.* 30:145-158; Hood and Cheresh (2002) *Nature Rev. Cancer* 2:91-100; Timme et al. (2003) *Curr. Drug Targets* 4:251-261; Robbins and Itzkowitz (2002) *Med. Clin. North Am.* 86:1467-1495; Grady and Markowitz (2002) *Annu. Rev. Genomics Hum. Genet.* 3:101-128; Bauer, et al. (2001) *Glia* 36:235-243; Stanimirovic and Satoh (2000) *Brain Pathol.* 10:113-126).

An endpoint of inhibition is generally 75% of the control or less, preferably 50% of the control or less, more preferably 25% of the control or less, and most preferably 10% of the control or less. Generally, an endpoint of activation is at least 150% the control, preferably at least two times the control, more preferably at least four times the control, and most preferably at least 10 times the control.

"Small molecule" is defined as a molecule with a molecular weight that is less than 10 kDa, typically less than 2 kDa, and preferably less than 1 kDa. Small molecules include, but are not limited to, inorganic molecules, organic molecules, organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules. Small molecules, such as peptide mimetics of antibodies and cytokines, as well as small molecule toxins are described. See, e.g., Casset et al. (2003) *Biochem. Biophys. Res. Commun.* 307:198-205; Muyldermans (2001) *J. Biotechnol.* 74:277-302; Li (2000) *Nat. Biotechnol.* 18:1251-1256; Apostolopoulos et al. (2002) *Curr. Med. Chem.* 9:411-420; Monfardini et al. (2002) *Curr. Pharm. Des.* 8:2185-2199; Domingues et al. (1999) *Nat. Struct. Biol.* 6:652-656; Sato and Sone (2003) *Biochem. J.* 371:603-608; U.S. Pat. No. 6,326,482.

"Specifically" or "selectively" binds, when referring to a ligand/receptor, antibody/antigen, or other binding pair, indicates a binding reaction that is determinative of the presence of the protein in a heterogeneous population of proteins and other biologics. Thus, under designated conditions, a specified ligand binds to a particular receptor and does not bind in a significant amount to other proteins present in the sample. As used herein, an antibody is said to bind specifically to a polypeptide comprising a given sequence (in this case GITR) if it binds to polypeptides comprising the sequence of GITR but does not bind to proteins lacking the sequence of GITR. For example, an antibody that specifically binds to a polypeptide comprising GITR may bind to a FLAG®-tagged form of GITR but will not bind to other FLAG®-tagged proteins.

The antibody, or binding composition derived from the antigen-binding site of an antibody, of the contemplated method binds to its antigen with an affinity that is at least two fold greater, preferably at least ten times greater, more preferably at least 20-times greater, and most preferably at least 100-times greater than the affinity with unrelated antigens. In a preferred embodiment the antibody will have an affinity that is greater than about $10^9$ liters/mol, as determined, e.g., by Scatchard analysis. Munsen et al. (1980) *Analyt. Biochem.* 107:220-239.

"Chronic viral infection" or "persistent viral infection" as used herein, is meant a viral infection of humans or other animals which is able to infect a host and reproduce within the cells of a host over a prolonged period of time—usually weeks, months or years, without proving fatal. Amongst viruses giving rise to chronic infections and which may be treated in accordance with the present invention are the human papilloma viruses (HPV), Herpes simplex and other herpes viruses, the viruses of hepatitis B and C (HBV and HCV) as well as other hepatitis viruses, the measles virus, all of which can produce important clinical diseases, and HIV. Prolonged infection may ultimately lead to the induction of disease which may be, e.g. in the case of hepatitis C virus liver cancer, fatal to the patient. Other chronic viral infections which may be treated in accordance with the present invention include Epstein Barr virus (EBV), as well as other viruses such as those which may be associated with tumors, or in the case of animals, various veterinary viral diseases, for example those of domestic pets or farmyard animals important in agriculture.

The term "antiviral activity" refers to an inhibition of viral transmission to uninfected cells, inhibition of the replication of a virus, prevention of the virus from establishing itself in a host, or ameliorating or alleviating the symptoms of the disease caused by viral infection. These effects can be evidenced by a reduction in viral load or decrease in mortality and/or morbidity, which assays are described infra. An antiviral agent or drug, has antiviral activity and is useful for treating persistent or chronic viral infections alone, or as part of a multi-drug combination therapy.

II. General

The present invention provides engineered anti-GITR antibodies and uses thereof to treat immune disorders, in particular impaired response to infectious diseases (including viral infections) and cancer.

GITR, also known as TNFRSF18, is a receptor belonging to the TNR-R superfamily. To date, crystal structures of human or mouse GITR are not available, however, a modular architecture of the molecule, based upon studies described, e.g., in Naismith and Sprang (1998) *Trends Biochem. Sci.* 23:74-79, can be established. FIG. 2 illustrates that human GITR can be divided into 6 modules. From the studies below, certain antibodies having agonist activity may have conformational epitopes that span modules 3 and 4.

II. Generation of GITR Specific Antibodies

Any suitable method for generating monoclonal antibodies may be used. For example, a recipient may be immunized with GITR or a fragment thereof. Any suitable method of immunization can be used. Such methods can include adjuvants, other immunostimulants, repeated booster immunizations, and the use of one or more immunization routes. Any suitable source of GITR can be used as the immunogen for the generation of the non-human antibody of the compositions and methods disclosed herein. Such forms include, but are not limited whole protein, peptide(s), and epitopes generated through recombinant, synthetic, chemical or enzymatic degradation means known in the art. In preferred embodiments the immunogen comprises the extracellular portion of GITR.

Any form of the antigen can be used to generate the antibody that is sufficient to generate a biologically active antibody. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may genomic or non-genomic (e.g., cDNA) and encodes at least a portion of the extracellular domain. As used herein, the term "portion" refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids.

Any suitable method can be used to elicit an antibody with the desired biologic properties to enhance GITR signaling. It is desirable to prepare monoclonal antibodies (mAbs) from various mammalian hosts, such as mice, rats, other rodents, humans, other primates, etc. Description of techniques for preparing such monoclonal antibodies may be found in, e.g., Stites et al. (eds.) BASIC AND CLINICAL IMMUNOLOGY (4th ed.) Lange Medical Publications, Los Altos, Calif., and references cited therein; Harlow and Lane (1988) ANTIBODIES: A LABORATORY MANUAL CSH Press; Goding (1986) MONOCLONAL ANTIBODIES: PRINCIPLES AND PRACTICE (2d ed.) Academic Press, New York, N.Y. Thus, monoclonal antibodies may be obtained by a variety of techniques familiar to researchers skilled in the art. Typically, spleen cells from an animal immunized with a desired antigen are immortalized, commonly by fusion with a myeloma cell. See Kohler and Milstein (1976) *Eur. J. Immunol.* 6:511-519. Alternative methods of immortalization include transformation with Epstein Barr Virus, oncogenes, or retroviruses, or other methods known in the art. See, e.g., Doyle et al. (eds. 1994 and periodic supplements) CELL AND TISSUE CULTURE: LABORATORY PROCEDURES, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences that encode a monoclonal antibody or a antigen binding fragment thereof by screening a DNA library from human B cells according, e.g., to the general protocol outlined by Huse et al. (1989) *Science* 246:1275-1281.

Other suitable techniques involve selection of libraries of antibodies in phage or similar vectors. See, e.g., Huse et al. supra; and Ward et al. (1989) *Nature* 341:544-546. The polypeptides and antibodies of the present invention may be used with or without modification, including chimeric or humanized antibodies. Frequently, the polypeptides and antibodies will be labeled by joining, either covalently or non-covalently, a substance that provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly U.S. Pat. No. 4,816,567; and Queen et al. (1989) *Proc. Nat'l Acad. Sci.* USA 86:10029-10033; or made in transgenic mice, see Mendez et al. (1997) *Nature Genetics* 15:146-156. See also Abgenix and Medarex technologies.

Alternatively, monoclonal antibodies can be produced by enrichment of clonal populations of B cells isolated from spleens of animals (e.g., mice, rats, rabbits, etc.) immunized with human GITR (see, e.g., WO2008045140, U.S. Pat. No. 5,627,052, and US20030186327).

Antibodies or binding compositions against predetermined fragments of GITR can be raised by immunization of animals with conjugates of the polypeptide, fragments, peptides, or epitopes with carrier proteins. Monoclonal antibodies are prepared from cells secreting the desired antibody. These antibodies can be screened for binding to normal or defective GITR. These monoclonal antibodies will usually bind with at least a $K_d$ of about 1 µM, more usually at least about 300 nM, 30 nM, 10 nM, 3 nM, 1 nM, 300 pM, 100 pM, 30 pM or better, usually determined by ELISA or Biacore. Suitable non-human antibodies may also be identified using the biologic assays described in Examples 5 and 6, below.

Hybridomas corresponding to clones 36E5, 3D6, 61G6, 6H6 and 61F6 were deposited at the American Type Culture Collection ("ATCC") under the Budapest Treaty requirements, as PTA-9890, PTA-9889, PTA-9891, PTA-9892, and PTA-9893, respectively, on Mar. 25, 2009.

Hybridomas corresponding to clones 1D8, 17F10, 35D8, 49A1, 9E5, and 31H6 were deposited at the ATCC in accordance with the Budapest Treaty requirements on Aug. 21, 2009, as PTA-10286, PTA-10287, PTA-10288, PTA-10289, PTA-10290, and PTA-10291.

IV. Humanization of GITR Specific Antibodies

Any suitable non-human antibody can be used as a source for the hypervariable region. Sources for non-human antibodies include, but are not limited to, murine (e.g. *Mus musculus*), rat (e.g. *Rattus norvegicus*), Lagomorphs (including rabbits), bovine, and primates. For the most part, humanized antibodies are human immunoglobulins (recipient antibody) in which hypervariable region residues of the recipient are replaced by hypervariable region residues from a non-human species (donor antibody) such as mouse, rat, rabbit or non-human primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance of the desired biological activity. For further details, see Jones et al. (1986) *Nature* 321:522-525; Reichmann et al. (1988) *Nature* 332:323-329; and Presta (1992) *Curr. Op. Struct. Biol.* 2:593-596.

Methods for recombinantly engineering antibodies have been described, e.g., by Boss et al. (U.S. Pat. No. 4,816,397), Cabilly et al. (U.S. Pat. No. 4,816,567), Law et al. (European Patent Application Publication No. 438310) and Winter (European Patent Application Publication No. 239400).

Amino acid sequence variants of humanized anti-GITR antibody are prepared by introducing appropriate nucleotide changes into the humanized anti-GITR antibody DNA, or by peptide synthesis. Such variants include, for example, deletions from, and/or insertions into, and/or substitutions of, residues within the amino acid sequences shown for the humanized anti-GITR antibody. Any combination of deletion, insertion, and substitution is made to arrive at the final construct, provided that the final construct possesses the desired characteristics. The amino acid changes also may alter post-translational processes of the humanized anti-GITR antibody, such as changing the number or position of glycosylation sites.

A useful method for identification of certain residues or regions of the humanized anti-GITR antibody polypeptide that are preferred locations for mutagenesis is called "alanine scanning mutagenesis," as described by Cunningham and Wells (1989) *Science* 244: 1081-1085. Here, a residue or group of target residues are identified (e.g., charged residues such as Arg, Asp, His, Lys, and Glu) and replaced by a neutral or negatively charged amino acid (most preferably alanine or polyalanine) to affect the interaction of the amino acids with GITR antigen. The amino acid residues demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, Ala scanning or random mutagenesis is conducted at the target codon or region and the expressed humanized anti-GITR antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include humanized anti-GITR antibody with an N-terminal methionyl residue or the antibody fused to an epitope tag. Other insertional variants of the humanized anti-GITR antibody molecule include the fusion to the N- or C-terminus of humanized anti-GITR antibody of an enzyme or a polypeptide that increases the serum half-life of the antibody.

Another type of variant is an amino acid substitution variant. These variants have at least one amino acid residue in the humanized anti-GITR antibody molecule removed and a different residue inserted in its place. The sites of greatest interest for substitutional mutagenesis include the hypervariable loops, but FR alterations are also contemplated.

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Yet another type of amino acid variant is the substitution of residues to provide for greater chemical stability of the final humanized antibody. For example, an asparagine (N) residue may be changed to reduce the potential for formation of isoaspartate at any NG sequences within a rodent CDR. A similar problem may occur at a DG sequence. Reissner and Aswad (2003) *Cell. Mol. Life. Sci.* 60:1281. Isoaspartate formation may debilitate or completely abrogate binding of an antibody to its target antigen. Presta (2005) *J. Allergy Clin. Immunol.* 116:731 at 734. In one embodiment, the asparagine is changed to glutamine (Q). In addition, methionine residues in rodent CDRs may be changed to reduce the possibility that the methionine sulfur would oxidize, which could reduce antigen binding affinity and also contribute to molecular heterogeneity in the final antibody preparation. Id. In one embodiment, the methionine is changed to alanine (A). Antibodies with such substitutions are subsequently screened to ensure that the substitutions do not decrease GITR binding affinity to unacceptable levels.

Nucleic acid molecules encoding amino acid sequence variants of humanized GITR specific antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-GITR antibody.

Ordinarily, amino acid sequence variants of the humanized anti-GITR antibody will have an amino acid sequence having at least 75% amino acid sequence identity with the original humanized antibody amino acid sequences of either the heavy or the light chain more preferably at least 80%, more preferably at least 85%, more preferably at least 90%, and most preferably at least 95%, 98% or 99%. Identity or homology with respect to this sequence is defined herein as the percentage of amino acid residues in the candidate sequence that are identical with the humanized anti-GITR residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology.

The humanized antibody can be selected from any class of immunoglobulins, including IgM, IgG, IgD, IgA, and IgE. Preferably, the antibody is an IgG antibody. Any isotype of IgG can be used, including $IgG_1$, $IgG_2$, $IgG_3$, and $IgG_4$. Variants of the IgG isotypes are also contemplated. The humanized antibody may comprise sequences from more than one class or isotype. Optimization of the necessary constant domain sequences to generate the desired biologic activity is readily achieved by screening the antibodies in the biological assays described in the Examples.

Likewise, either class of light chain can be used in the compositions and methods herein. Specifically, kappa, lambda, or variants thereof are useful in the present compositions and methods.

Any suitable portion of the CDR sequences from the non-human antibody can be used. The CDR sequences can be mutagenized by substitution, insertion or deletion of at least one residue such that the CDR sequence is distinct from the human and non-human antibody sequence employed. It is contemplated that such mutations would be minimal. Typically, at least 75% of the humanized antibody residues will correspond to those of the non-human CDR residues, more often 90%, and most preferably greater than 95%.

Any suitable portion of the FR sequences from the human antibody can be used. The FR sequences can be mutagenized by substitution, insertion or deletion of at least one residue such that the FR sequence is distinct from the human and non-human antibody sequence employed. It is contemplated that such mutations would be minimal. Typically, at least 75% of the humanized antibody residues will correspond to those of the human FR residues, more often 90%, and most preferably greater than 95%, 98% or 99%.

CDR and FR residues are determined according to the standard sequence definition of Kabat. Kabat et al. (1987) Sequences of Proteins of Immunological Interest, National Institutes of Health, Bethesda Md. SEQ ID NOs: 1-11 show the heavy chain variable domain sequences of various rodent anti-human GITR antibodies, and SEQ ID NOs: 12-22 depict the light chain variable domain sequences.

TABLE 2

Heavy Chain Sequences and Domains

| ANTIBODY CLONE | SEQ ID NO: | $V_H$ RESIDUES | HEAVY CHAIN CDR RESIDUES | | |
|---|---|---|---|---|---|
| | | | CDR-H1 | CDR-H2 | CDR-H3 |
| 36H5 | 1 | 1-118 | 26-35 | 50-65 | 98-107 |
| 3D6 | 2 | 1-123 | 26-35 | 50-66 | 99-112 |
| 61G6 | 3 | 1-118 | 26-36 | 51-66 | 99-107 |
| 6H6 | 4 | 1-118 | 26-35 | 50-66 | 99-107 |
| 61F6 | 5 | 1-119 | 26-35 | 50-66 | 99-108 |
| 1D8 | 6 | 1-122 | 26-37 | 52-67 | 100-111 |
| 17F10 | 7 | 1-117 | 26-35 | 50-65 | 98-106 |
| 35D8 | 8 | 1-120 | 26-35 | 50-65 | 98-109 |
| 49A1 | 9 | 1-120 | 26-35 | 50-65 | 98-109 |
| 9E5 | 10 | 1-121 | 26-37 | 52-67 | 100-110 |
| 31H6 | 11 | 1-121 | 26-37 | 52-67 | 100-110 |

TABLE 3

Light Chain sequences and Domains

| ANTIBODY CLONE | SEQ ID NO: | $V_L$ RESIDUES | LIGHT CHAIN CDR RESIDUES | | |
|---|---|---|---|---|---|
| | | | CDR-L1 | CDR-L2 | CDR-L3 |
| 36H5 | 12 | 1-113 | 24-39 | 54-60 | 93-101 |
| 3D6 | 13 | 1-113 | 24-39 | 55-61 | 94-102 |
| 61G6 | 14 | 1-108 | 24-33 | 49-55 | 88-96 |
| 6H6 | 15 | 1-110 | 24-35 | 51-57 | 90-98 |
| 61F6 | 16 | 1-113 | 24-38 | 54-60 | 93-101 |
| 1D8 | 17 | 1-118 | 24-39 | 55-61 | 94-102 |
| 17F10 | 18 | 1-113 | 24-34 | 50-56 | 89-97 |
| 35D8 | 19 | 1-114 | 24-34 | 50-56 | 89-98 |
| 49A1 | 20 | 1-114 | 24-34 | 50-56 | 89-98 |
| 9E5 | 21 | 1-113 | 24-34 | 50-56 | 89-97 |
| 31H6 | 22 | 1-113 | 24-34 | 50-56 | 89-97 |

In one embodiment, CDRs include variants of any single sequence CDR disclosed herein (SEQ ID NOs: 23-88), in which the variant comprises 1, 2, 3, 4, 5, 6, 7, 8, 9, or more conservative amino acid substitutions relative to the disclosed sequence, as determined using the data of Table 1.

Also contemplated are chimeric antibodies. As noted above, typical chimeric antibodies comprise a portion of the heavy and/or light chain identical with, or homologous to, corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. See U.S. Pat. No. 4,816,567; and Morrison et al. (1984)*Proc. Natl. Acad. Sci.* USA 81: 6851-6855.

Bispecific antibodies are also useful in the present methods and compositions. As used herein, the term "bispecific antibody" refers to an antibody, typically a monoclonal antibody, having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al. (1983) *Nature* 305: 537-39. Alternatively, bispecific antibodies can be prepared using chemical linkage. See, e.g., Brennan et al. (1985) *Science* 229:81. Bispecific antibodies include bispecific antibody fragments. See, e.g., Holliger et al. (1993) *Proc. Natl. Acad. Sci. U.S.A.* 90:6444-48, Gruber et al. (1994) *J. Immunol.* 152:5368.

In yet other embodiments, different constant domains may be appended to humanized $V_L$ and $V_H$ regions derived from the CDRs provided herein. For example, if a particular intended use of an antibody (or fragment) of the present invention were to call for altered effector functions, a heavy chain constant domain other than IgG1 may be used. Although IgG1 antibodies provide for long half-life and for effector functions, such as complement activation and antibody-dependent cellular cytotoxicity, such activities may not be desirable for all uses of the antibody. In such instances an IgG4 or IgG2 constant domain, for example, may be used.

The parental and engineered forms of the antibodies of the present invention may also be conjugated to a chemical moiety. The chemical moiety may be, inter alia, a polymer, a radionuclide or a cytotoxic factor. Preferably the chemical moiety is a polymer which increases the half-life of the antibody molecule in the body of a subject. Suitable polymers include, but are not limited to, polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee et al., (1999) (Bioconj. Chem. 10:973-981) discloses PEG conjugated single-chain antibodies. Wen et al., (2001) (Bioconj. Chem. 12:545-553) disclose conjugating antibodies with PEG which is attached to a radiometal chelator (diethylenetriaminpentaacetic acid (DTPA)).

The antibodies and antibody fragments or the GITR soluble proteins or fragments thereof of the invention may also be conjugated with labels such as $^{99}Tc$, $^{90}Y$, $^{111}In$, $^{32}P$, $^{14}C$, $^{125}I$, $^{3}H$, $^{131}I$, $^{11}C$, $^{15}O$, $^{13}N$, $^{18}F$, $^{35}S$, $^{51}Cr$, $^{57}To$, $^{226}Ra$, $^{60}Co$, $^{59}Fe$, $^{57}Se$, $^{152}Eu$, $^{67}CU$, $^{217}Ci$, $^{211}At$, $^{212}Pb$, $^{47}Sc$, $^{109}Pd$, $^{234}Th$, and $^{40}K$, $^{157}Gd$, $^{55}Mn$, $^{52}Tr$ and $^{56}Fe$.

The antibodies and antibody fragments or the GITR soluble proteins or fragments thereof of the invention may also be conjugated with fluorescent or chemilluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}Eu$, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

Any method known in the art for conjugating the antibody molecules or protein molecules of the invention to the various moieties may be employed, including those methods described by Hunter et al., (1962) Nature 144:945; David et al., (1974) Biochemistry 13:1014; Pain et al., (1981) J. Immunol. Meth. 40:219; and Nygren, J., (1982) Histochem. and Cytochem. 30:407. Methods for conjugating antibodies and proteins are conventional and very well known in the art.

V. Biological Activity of Humanized Anti-GITR Antibodies

Antibodies having the characteristics identified herein as being desirable in a humanized anti-GITR antibody can be screened for inhibitory biologic activity in vitro or suitable binding affinity. Agonist antibodies may be distinguished from antagonist antibodies using the biological assay provided at Example 5. Antibodies that exhibit agonist activity will not block the activity of GITR, but will instead stimulate the response typically mediated by GITR signaling.

To screen for antibodies that bind to the epitope on human GITR bound by an antibody of interest (e.g., those that block binding of GITR), a routine cross-blocking assay such as that described in ANTIBODIES, A LABORATORY MANUAL, Cold Spring Harbor Laboratory, Ed Harlow and David Lane (1988), can be performed. Antibodies that bind to the same epitope are likely to cross-block in such assays, but not all cross-blocking antibodies will necessarily bind at precisely the same epitope since cross-blocking may result from steric hindrance of antibody binding by antibodies bind at overlapping epitopes, or even nearby non-overlapping epitopes.

Alternatively, epitope mapping, e.g., as described in Champe et al. (1995) *J. Biol. Chem.* 270:1388-1394, can be performed to determine whether the antibody binds an epitope of interest. "Alanine scanning mutagenesis," as described by Cunningham and Wells (1989) *Science* 244: 1081-1085, or some other form of point mutagenesis of amino acid residues in human GITR may also be used to determine the functional epitope for an anti-GITR antibody of the present invention. Mutagenesis studies, however, may also reveal amino acid residues that are crucial to the overall three-dimensional structure of GITR but that are not directly involved in antibody-antigen contacts, and thus other methods may be necessary to confirm a functional epitope determined using this method.

The epitope bound by a specific antibody may also be determined by assessing binding of the antibody to peptides comprising fragments of human GITR (SEQ ID NO: 41). A series of overlapping peptides encompassing the sequence of GITR may be synthesized and screened for binding, e.g. in a direct ELISA, a competitive ELISA (where the peptide is assessed for its ability to prevent binding of an antibody to GITR bound to a well of a microtiter plate), or on a chip. Such peptide screening methods may not be capable of detecting some discontinuous functional epitopes, i.e. functional epitopes that involve amino acid residues that are not contiguous along the primary sequence of the GITR polypeptide chain.

The epitope bound by antibodies of the present invention may also be determined by structural methods, such as X-ray crystal structure determination (e.g., WO2005/044853), molecular modeling and nuclear magnetic resonance (NMR) spectroscopy, including NMR determination of the H-D exchange rates of labile amide hydrogens in GITR when free and when bound in a complex with an antibody of interest (Zinn-Justin et al. (1992) *Biochemistry* 31:11335-11347; Zinn-Justin et al. (1993) *Biochemistry* 32:6884-6891).

With regard to X-ray crystallography, crystallization may be accomplished using any of the known methods in the art (e.g. Giege et al. (1994) *Acta Crystallogr.* D50:339-350; McPherson (1990) *Eur. J. Biochem.* 189:1-23), including microbatch (e.g. Chayen (1997) *Structure* 5:1269-1274), hanging-drop vapor diffusion (e.g. McPherson (1976) *J. Biol. Chem.* 251:6300-6303), seeding and dialysis. It is desirable to use a protein preparation having a concentration of at least about 1 mg/mL and preferably about 10 mg/mL to about 20 mg/mL. Crystallization may be best achieved in a precipitant solution containing polyethylene glycol 1000-20,000 (PEG; average molecular weight ranging from about 1000 to about 20,000 Da), preferably about 5000 to about 7000 Da, more preferably about 6000 Da, with concentrations ranging from about 10% to about 30% (w/v). It may also be desirable to include a protein stabilizing agent, e.g. glycerol at a concentration ranging from about 0.5% to about 20%. A suitable salt, such as sodium chloride, lithium chloride or sodium citrate may also be desirable in the precipitant solution, preferably in a concentration ranging from about 1 mM to about 1000 mM. The precipitant is preferably buffered to a pH of from about 3.0 to about 5.0, preferably about 4.0. Specific buffers useful in the precipitant solution may vary and are well-known in the art. Scopes, Protein Purification: Principles and Practice, Third ed., (1994) Springer-Verlag, New York. Examples of useful buffers include, but are not limited to, HEPES, Tris, MES and acetate. Crystals may be grow at a wide range of temperatures, including 2° C., 4° C., 8° C. and 26° C.

Antibody:antigen crystals may be studied using well-known X-ray diffraction techniques and may be refined using computer software such as X-PLOR (Yale University, 1992, distributed by Molecular Simulations, Inc.; see e.g. Blundell & Johnson (1985) *Meth. Enzymol.* 114 & 115, H. W. Wyckoff et al. eds., Academic Press; U.S. Patent Application Publication No. 2004/0014194), and BUSTER (Bricogne (1993) *Acta Cryst.* D49:37-60; Bricogne (1997) *Meth. Enzymol.* 276A:361-423, Carter & Sweet, eds.; Roversi et al. (2000) *Acta Cryst.* D56:1313-1323).

Additional antibodies binding to the same epitope as an antibody of the present invention may be obtained, for example, by screening of antibodies raised against GITR for binding to the epitope, or by immunization of an animal with a peptide comprising a fragment of human GITR comprising the epitope sequence. Antibodies that bind to the same functional epitope might be expected to exhibit similar biological activities, such as blocking receptor binding, and such activities can be confirmed by functional assays of the antibodies.

Antibody affinities may be determined using standard analysis. Preferred humanized antibodies are those that bind human GITR with a $K_d$ value of no more than about $1 \times 10^{-7}$; preferably no more than about $1 \times 10^{-8}$; more preferably no more than about $1 \times 10^{-9}$; and most preferably no more than about $1 \times 10^{-10}$ or even $1 \times 10^{-11}$ M.

The antibodies and fragments thereof useful in the present compositions and methods are biologically active antibodies and fragments. As used herein, the term "biologically active" refers to an antibody or antibody fragment that is capable of binding the desired the antigenic epitope and directly or indirectly exerting a biologic effect. As used herein, the term "specific" refers to the selective binding of the antibody to the target antigen epitope. Antibodies can be tested for specificity of binding by comparing binding to GITR to binding to irrelevant antigen or antigen mixture under a given set of conditions. If the antibody binds to GITR at least 10, and preferably 50 times more than to irrelevant antigen or antigen mixture then it is considered to be specific. An antibody that "specifically binds" to GITR does not bind to proteins that do not comprise the GITR-derived sequences, i.e. "specificity" as used herein relates to GITR specificity, and not any other sequences that may be present in the protein in question. For example, as used herein, an antibody that "specifically binds" to a polypeptide comprising GITR will typically bind to FLAG®-GITR, which is a fusion protein comprising GITR and a FLAG® peptide tag, but it does not bind to the FLAG® peptide tag alone or when it is fused to a protein other than GITR.

GITR-specific binding compounds of the present invention, such as agonistic GITR specific antibodies, can enhance its biological activity in any manner, including but not limited to increasing the immune response to a microbial infection.

VI. Pharmaceutical Compositions

To prepare pharmaceutical or sterile compositions including GITR antibody, the cytokine analogue or mutein, antibody thereto, or nucleic acid thereof, is admixed with a pharmaceutically acceptable carrier or excipient. See, e.g., *Remington's Pharmaceutical Sciences and U.S. Pharmacopeia: National Formulary*, Mack Publishing Company, Easton, Pa. (1984).

Formulations of therapeutic and diagnostic agents may be prepared by mixing with physiologically acceptable carriers, excipients, or stabilizers in the form of, e.g., lyophilized powders, slurries, aqueous solutions or suspensions. See, e.g., Hardman et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis et al. (eds.) (1993) *Pharmaceutical Dosage Forms Parenteral Medications*, Marcel Dekker, NY; Lieberman, et al. (eds.) (1990) *Pharmaceutical Dosage Forms: Tablets*, Marcel Dekker, NY; Lieberman et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.

Toxicity and therapeutic efficacy of the antibody compositions, administered alone or in combination with an immunosuppressive agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio of $LD_{50}$ to $ED_{50}$. Antibodies exhibiting high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

The mode of administration is not particularly important. Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of antibody used in the pharmaceutical composition or to practice the method of the present invention can be carried out in a variety of conventional ways, such as oral ingestion, inhalation, topical application or cutaneous, subcutaneous, intraperitoneal, parenteral, intraarterial or intravenous injection.

Alternately, one may administer the antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

Selecting an administration regimen for a therapeutic depends on several factors, including the serum or tissue turnover rate of the entity, the level of symptoms, the immunogenicity of the entity, and the accessibility of the target cells in the biological matrix. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies*, Cytokines and Arthritis, Marcel Dekker, New York, N.Y.; Bach (ed.) (1993) *Monoclonal Antibodies and*

*Peptide Therapy in Autoimmune Diseases*, Marcel Dekker, New York, N.Y.; Baert et al. (2003) *New Engl. J. Med.* 348: 601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602.

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is substantially derived from the same species as the animal targeted for treatment (e.g. a humanized antibody for treatment of human subjects), thereby minimizing any immune response to the reagent.

Antibodies, antibody fragments, and cytokines can be provided by continuous infusion, or by doses at intervals of, e.g., one day, 1-7 times per week, one week, two weeks, monthly, bimonthly, etc. Doses may be provided intravenously, subcutaneously, topically, orally, nasally, rectally, intramuscular, intracerebrally, intraspinally, or by inhalation. A preferred dose protocol is one involving the maximal dose or dose frequency that avoids significant undesirable side effects. A total weekly dose is generally at least 0.05 µg/kg, 0.2 µg/kg, 0.5 µg/kg, 1 µg/kg, 10 µg/kg, 100 µg/kg, 0.2 mg/kg, 1.0 mg/kg, 2.0 mg/kg, 10 mg/kg, 25 mg/kg, 50 mg/kg body weight or more. See, e.g., Yang et al. (2003)*New Engl. J. Med.* 349:427-434; Herold et al. (2002) *New Engl. J. Med.* 346: 1692-1698; Liu et al. (1999) *J. Neurol. Neurosurg. Psych.* 67:451-456; Portielji et al. (20003) *Cancer Immunol. Immunother.* 52:133-144. The desired dose of a small molecule therapeutic, e.g., a peptide mimetic, natural product, or organic chemical, is about the same as for an antibody or polypeptide, on a moles/kg basis.

As used herein, "inhibit" or "treat" or "treatment" includes a postponement of development of the symptoms associated with autoimmune disease or pathogen-induced immunopathology and/or a reduction in the severity of such symptoms that will or are expected to develop. The terms further include ameliorating existing uncontrolled or unwanted autoimmune-related or pathogen-induced immunopathology symptoms, preventing additional symptoms, and ameliorating or preventing the underlying causes of such symptoms. Thus, the terms denote that a beneficial result has been conferred on a vertebrate subject with an autoimmune or pathogen-induced immunopathology disease or symptom, or with the potential to develop such a disease or symptom.

As used herein, the term "therapeutically effective amount" or "effective amount" refers to an amount of an GITR-specific binding compound, e.g. and antibody, that when administered alone or in combination with an additional therapeutic agent to a cell, tissue, or subject is effective to prevent or ameliorate the autoimmune disease or pathogen-induced immunopathology associated disease or condition or the progression of the disease. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of therapeutic will decrease the symptoms typically by at least 10%; usually by at least 20%; preferably at least about 30%; more preferably at least 40%, and most preferably by at least 50%.

Methods for co-administration or treatment with a second therapeutic agent, e.g., a cytokine, antibody, steroid, chemotherapeutic agent, antibiotic, anti-viral, or radiation, are well known in the art, see, e.g., Hardman et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., PA; Chabner and Longo (eds.) (2001) Cancer Chemotherapy and Biotherapy, Lippincott, Williams & Wilkins, Phila., PA.

Chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1l (see, e.g., Agnew, *Chem. Intl. Ed. Engl.,* 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene;

edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; XELODA® capecitabine; ibandronate; CPT-11; topoisomerase inhibitor RFS 2000; difluoromethylornithine (DMFO); retinoids such as retinoic acid; and pharmaceutically acceptable salts, acids or derivatives of any of the above.

Also included are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON. toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

In particular, transforming growth factor (TGF)-β displays an array of pleiotropic effects in cellular functions such as proliferation, homeostasis, angiogenesis and wound healing. Aberrant regulation of TGF-β function contributes to cancer progression. Most cancers are characterized by excessive transforming growth factor-β production by tumors, which can promote tumor growth and mediate epithelial-to-mesenchymal transition. TGF-β also plays a pivotal role within the immune system maintaining tolerance via the regulation of lymphocyte proliferation, differentiation, and survival. TGF-β has been proven to be an important suppressive element in enhancing Treg function and dampening tumor immunity. Administration of TGF-β inhibitors in conjunction with GITR agonists, e.g., antibodies, is contemplated.

Also contemplated is co-administration with anti-viral therapeutics. Anti-virals include any drug that destroys viruses. Antivirals may include interferons which function to inhibit replication of the virus, protease inhibitors, and reverse transcriptase inhibitors or agents contained in the combination of highly active antiretroviral therapy (HAART) for HIV.

Typical veterinary, experimental, or research subjects include monkeys, dogs, cats, rats, mice, rabbits, guinea pigs, horses, and humans.

VII. Antibody Production

In one embodiment, for recombinant production of the antibodies of the present invention, the nucleic acids encoding the two chains are isolated and inserted into one or more replicable vectors for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence. In one embodiment, both the light and heavy chains of a humanized anti-GITR antibody of the present invention are expressed from the same vector, e.g. a plasmid or an adenoviral vector.

Antibodies of the present invention may be produced by any method known in the art. In one embodiment, antibodies are expressed in mammalian or insect cells in culture, such as Chinese hamster ovary (CHO) cells, human embryonic kidney (HEK) 293 cells, mouse myeloma NSO cells, baby hamster kidney (BHK) cells, *Spodoptera frugiperda* ovarian (Sf9) cells. In one embodiment, antibodies secreted from CHO cells are recovered and purified by standard chromatographic methods, such as protein A, cation exchange, anion exchange, hydrophobic interaction, and hydroxyapatite chromatography. Resulting antibodies are concentrated and stored in 20 mM sodium acetate, pH 5.5.

In another embodiment, the antibodies of the present invention are produced in yeast according to the methods described in WO2005/040395. Briefly, vectors encoding the individual light or heavy chains of an antibody of interest are introduced into different yeast haploid cells, e.g. different mating types of the yeast *Pichia pastoris*, which yeast haploid cells are optionally complementary auxotrophs. The transformed haploid yeast cells can then be mated or fused to give a diploid yeast cell capable of producing both the heavy and the light chains. The diploid strain is then able to secret the fully assembled and biologically active antibody. The relative expression levels of the two chains can be optimized, for example, by using vectors with different copy number, using transcriptional promoters of different strengths, or inducing expression from inducible promoters driving transcription of the genes encoding one or both chains.

In one embodiment, the respective heavy and light chains of a plurality of different anti-GITR antibodies (the "original" antibodies) are introduced into yeast haploid cells to create a library of haploid yeast strains of one mating type expressing a plurality of light chains, and a library of haploid yeast strains of a different mating type expressing a plurality of heavy chains. These libraries of haploid strains can be mated (or fused as spheroplasts) to produce a series of diploid yeast cells expressing a combinatorial library of antibodies comprised of the various possible permutations of light and heavy chains. The combinatorial library of antibodies can then be screened to determine whether any of the antibodies has properties that are superior (e.g. higher affinity for GITR) to those of the original antibodies. See. E.g., WO2005/040395.

In another embodiment, antibodies of the present invention are human domain antibodies in which portions of an antibody variable domain are linked in a polypeptide of molecular weight approximately 13 kDa. See, e.g., U.S. Pat. Publication No. 2004/0110941. Such single domain, low molecular weight agents provide numerous advantages in terms of ease of synthesis, stability, and route of administration.

VIII. Uses

The present invention provides methods for using anti-GITR antibodies and fragments thereof for the treatment and diagnosis of proliferative or inflammatory disorders and conditions.

The present invention provides methods for diagnosing the presence of a microbial infection or cancer by analyzing expression levels of GITR in test cells, tissue or bodily fluids compared with GITR levels in cells, tissues or bodily fluids of preferably the same type from a control. As demonstrated herein, an increase in level of GITR expression, for example, in the patient versus the control is associated with the presence of cancer.

Typically, for a quantitative diagnostic assay, a positive result indicating the patient tested has cancer or an infectious disease, is one in which the cells, tissues, or bodily fluids has an GITR expression level at least two times higher, five times higher, ten times higher, fifteen times higher, twenty times higher, twenty-five times higher.

Assay techniques that may be used to determine levels of gene and protein expression, such as GITR, of the present inventions, in a sample derived from a host are well known to those of skill in the art. Such assay methods include radioimmunoassays, reverse transcriptase PCR(RT-PCR) assays, quantitative real-time PCR assays, immunohistochemistry assays, in situ hybridization assays, competitive-binding assays, western blot assays, ELISA assays, and flow cytometric assays, for example, two color FACS analysis for M2 versus M1 phenotyping of tumor-associated macrophages (Mantovani et al., (2002) TRENDS in Immunology 23:549-555).

An ELISA assay initially comprises preparing an antibodies of the present invention, specific to GITR, preferably 36E5, 3D6, 61G6, 6H6, 61F6, 1D8, 17F10, 35D8, 49A1, 9E5, and 31H6 (collectively "GITR antibodies"). In addition, a reporter antibody generally is prepared that binds specifically to GITR. The reporter antibody is attached to a detectable reagent such as radioactive, fluorescent or an enzymatic reagent, for example horseradish peroxidase enzyme or alkaline phosphatase.

To carry out the ELISA, at least one of the GITR antibodies described above is incubated on a solid support, e.g., a polystyrene dish that binds the antibody. Any free protein binding sites on the dish are then covered by incubating with a non-specific protein, such as bovine serum albumin. Next, the sample to be analyzed is incubated in the dish, during which time GITR binds to the specific GITR antibody attached to the polystyrene dish. Unbound sample is washed out with buffer. A reporter antibody specifically directed to GITR and linked to horseradish peroxidase is placed in the dish resulting in binding of the reporter antibody to any monoclonal antibody bound to GITR. Unattached reporter antibody is then washed out. Reagents for peroxidase activity, including a calorimetric substrate are then added to the dish. Immobilized peroxidase, linked to GITR antibodies, produces a colored reaction product. The amount of color developed in a given time period is proportional to the amount of GITR protein present in the sample. Quantitative results typically are obtained by reference to a standard curve.

A competition assay may be employed wherein antibodies specific to GITR are attached to a solid support and labeled GITR and a sample derived from the host are passed over the solid support and the amount of label detected attached to the solid support can be correlated to a quantity of GITR in the sample.

The above tests may be carried out on samples derived from a variety of cells, bodily fluids and/or tissue extracts such as homogenates or solubilized tissue obtained from a patient. Tissue extracts are obtained routinely from tissue biopsy and autopsy material. Bodily fluids useful in the present invention include blood, urine, saliva or any other bodily secretion or derivative thereof. The term "blood" is meant to include whole blood, plasma, serum or any derivative of blood.

Antibodies of the present invention may be used to treat viral infections. HIV infection is characterized by defects in the generation and maintenance of central memory cells. CD8+ central memory cells have a shorter half-life and are less abundant in HIV-infected individuals than in controls. Also, the frequency of both CD4+ and CD8+ HIV-specific T cells decreases rapidly after initiation of highly active antiretroviral therapy (HAART). Co-stimulation on CD4+ by anti-GITR may provide a mechanism to increase memory CD8+ response and to contribute to clearance of the virus. It has been shown that treatment of persistently Friend virus-infected mice with anti-GITR antibody to ameliorate suppression by Tregs significantly improved IFN-γ production by the CD8+ T cells and allowed a significant reduction in viral loads (Dittmer et al., (2004) *Immunity* 20: 293-303).

Another characteristic of HIV infection is massive apoptosis of CD4+ T cells starting early in HIV infection. The progressive apoptotic deletion of CD4 T cells contributes to weakened HIV-specific cellular immune responses and to the development of AIDS. GITR co-stimulation has been shown to enhance murine antigen-specific cytokine secretion by protecting T cells from apoptosis. Lahey et al. (2007) *J Infect Dis.* 196: 43-49) demonstrated that anti-GITR treatment of HIV-specific CD4+ T cells enhances their cytokine expression and protects them from apoptosis.

For infections resulting from viral causes, the antibodies of the invention may be combined by application simultaneous with, prior to or subsequent to application of standard therapies for treating viral infections. Such standard therapies vary depending upon type of virus, although in almost all cases, administration of human serum containing antibodies (e.g., IgA, IgG) specific to the virus can be effective.

Influenza infection results in fever, cough, myalgia, headache and malaise, which often occur in seasonal epidemics. Influenza is also associated with a number of postinfectious disorders, such as encephalitis, myopericarditis, Goodpasture's syndrome, and Reye's syndrome. Influenza infection also suppresses normal pulmonary antibacterial defenses, such that patient's recovering from influenza have an increased risk of developing bacterial pneumonia.

Influenza viral surface proteins show marked antigenic variation, resulting from mutation and recombination. Thus, cytolytic T lymphocytes are the host's primary vehicle for the elimination of virus after infection. Influenza is classified into three primary types: A, B and C. Influenza A is unique in that it infects both humans and many other animals (e.g., pigs, horses, birds and seals) and is the principal cause of pandemic influenza. Also, when a cell is infected by two different influenza A strains, the segmented RNA genomes of two two parental virus types mix during replication to create a hybrid replicant, resulting in new epidemic strains. Influenza B does not replicate in animals and thus has less genetic variation and influenza C has only a single serotype.

Most conventional therapies are palliatives of the symptoms resulting from infection, while the host's immune response actually clears the disease. However, certain strains (e.g., influenza A) can cause more serious illness and death. Influenza A may be treated both clinically and prophylactically by the administration of the cyclic amines inhibitors amantadine and rimantadine, which inhibit viral replication. However, the clinical utility of these drugs is limited due to the relatively high incidence of adverse reactions, their narrow anti-viral spectrum (influenza A only), and the propensity of the virus to become resistant. The administration of serum IgG antibody to the major influenza surface proteins, hemagglutinin and neuraminidase can prevent pulmonary infection, whereas mucosal IgA is required to prevent infection of the upper respiratory tract and trachea. The most effective current treatment for influenza is vaccination with the administration of virus inactivated with formalin or β-propiolactone.

After an incubation of 9-11 days, hosts infected with the measles virus develop fever, cough, coryza and conjunctivitis. Within 1-2 days, an erythematous, maculopapular rash develop, which quickly spreads over the entire body. Because infection also suppresses cellular immunity, the host is at greater risk for developing bacterial superinfections, including otitis media, pneumonia and postinfectious encephalomyelitis. Acute infection is associated with significant morbidity and mortality, especially in malnourished adolescents.

Treatment for measles includes the passive administration of pooled human IgG, which can prevent infection in non-immune subjects, even if given up to one week after exposure. However, prior immunization with live, attenuated virus is the most effective treatment and prevents disease in more than 95% of those immunized. As there is one serotype of this virus, a single immunization or infection typically results in protection for life from subsequent infection.

In a small proportion of infected hosts, measles can develop into SSPE, which is a chronic progressive neurologic disorder resulting from a persistent infection of the central nervous system. SSPE is caused by clonal variants of measles virus with defects that interfere with virion assembly and budding. For these patients, reactivation of T-cells with the antibodies of the invention so as to facilitate viral clearance would be desirable.

Hepatitis B virus (HB-V) is the most infectious known bloodborne pathogen. It is a major cause of acute and chronic heptatis and hepatic carcinoma, as well as life-long, chronic infection. Following infection, the virus replicates in hepatocytes, which also then shed the surface antigen HBsAg. The detection of excessive levels of HBsAg in serum is used a standard method for diagnosing a hepatitis B infection. An acute infection may resolve or it can develop into a chronic persistent infection.

Current treatments for chronic HBV include α-inteferon, which increases the expression of class I human leukocyte antigen (HLA) on the surface of hepatocytes, thereby facilitating their recognition by cytotoxic T lymphocytes. Additionally, the nucleoside analogs ganciclovir, famciclovir and lamivudine have also shown some efficacy in clinical trial. Additional treatments for HBV infection include pegylated α-interferon, adenfovir, entecavir and telbivudine. While passive immunity can be conferred through parental administration of anti-HBsAg serum antibodies, vaccination with inactivated or recombinant HBsAg also confers resistance to infection. The antibodies of the invention may be combined with conventional treatments for hepatitis B infections for therapeutic advantage.

Hepatitis C virus (HC-V) infection may lead to a chronic form of hepatitis, resulting in cirrosis. While symptoms are similar to infections resulting from Hepatitis B, in distinct contrast to HB-V, infected hosts can be asymptomatic for 10-20 years. Treatment for HC-V infection includes the administration of a combination of α-interferon and ribavirin. A promising potential therapy for HC-V infection is the protease inhibitor telaprevir (VX-960). Additional treatments include: anti-PD-1 antibody (MDX-1106, Medarex), bavituximab (an antibody that binds anionic phospholipid phosphatidylserine in a B2-glycoprotein I dependent manner, Peregrine Pharmaceuticals), anti-HPV viral coat protein E2 antibod(y)(ies) (E.g., ATL 6865–Ab68+Ab65, XTL Pharmaceuticals) and Civacir® (polyclonal anti-HCV human immune globulin). The antibodies of the invention may be combined with one or more of these treatments for hepatitis C infections for therapeutic advantage.

The broad scope of this invention is best understood with reference to the following examples, which are not intended to limit the inventions to the specific embodiments. The specific embodiments described herein are offered by way of example only, and the invention is to be limited by the terms of the appended claims, along with the full scope of equivalents to which such claims are entitled.

EXAMPLES

Example 1

General Methods

Standard methods in molecular biology are described. Maniatis et al. (1982) *Molecular Cloning, A Laboratory Manual*, Cold Spring Harbor Laboratory Press, Cold Spring Harbor, N.Y.; Sambrook and Russell (2001) *Molecular Cloning, $3^{rd}$ ed.*, Cold Spring Harbor Laboratory Press, Cold Spring Harbor, N.Y.; Wu (1993) *Recombinant DNA*, Vol. 217, Academic Press, San Diego, Calif. Standard methods also appear in Ausbel et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described. Coligan et al. (2000) *Current Protocols in Protein Science*, Vol. 1, John Wiley and Sons, Inc., New York. Chemical analysis, chemical modification, post-translational modification, production of fusion proteins, glycosylation of proteins are described. See, e.g., Coligan et al. (2000) *Current Protocols in Protein Science*, Vol. 2, John Wiley and Sons, Inc., New York; Ausubel et al. (2001) *Current Protocols in Molecular Biology*, Vol. 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391. Production, purification, and fragmentation of polyclonal and monoclonal antibodies are described. Coligan et al. (2001) *Current Protcols in Immunology*, Vol. 1, John Wiley and Sons, Inc., New York; Harlow and Lane (1999) *Using Antibodies*, Cold Spring Harbor Laboratory Press, Cold Spring Harbor, N.Y.;

Harlow and Lane, supra. Standard techniques for characterizing ligand/receptor interactions are available. See, e.g., Coligan et al. (2001) *Current Protcols in Immunology*, Vol. 4, John Wiley, Inc., New York.

Methods for flow cytometry, including fluorescence activated cell sorting detection systems (FACS®), are available. See, e.g., Owens et al. (1994) *Flow Cytometry Principles for Clinical Laboratory Practice*, John Wiley and Sons, Hoboken, N.J.; Givan (2001) *Flow Cytometry*, $2^{nd}$ ed.; Wiley-Liss, Hoboken, N.J.; Shapiro (2003) *Practical Flow Cytometry*, John Wiley and Sons, Hoboken, N.J. Fluorescent reagents suitable for modifying nucleic acids, including nucleic acid primers and probes, polypeptides, and antibodies, for use, e.g., as diagnostic reagents, are available. Molecular Probes (2003) *Catalogue*, Molecular Probes, Inc., Eugene, Oreg.; Sigma-Aldrich (2003) *Catalogue*, St. Louis, Mo.

Standard methods of histology of the immune system are described. See, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.

Software packages and databases for determining, e.g., antigenic fragments, leader sequences, protein folding, functional domains, glycosylation sites, and sequence alignments, are available. See, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne et al. (2000) *Bioinformatics* 16: 741-742; Menne et al. (2000) *Bioinformatics Applications Note* 16:741-742; Wren et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690.

Example 2

Humanization of Anti-Human GITR Antibodies

The humanization of antibodies is described generally, e.g., in PCT patent application publications WO 2005/047324 and WO 2005/047326.

Briefly, the amino acid sequence of the non-human VH domain (e.g. SEQ ID NOs: 1-11) is compared to a group of five human VH germline amino acid sequences; one representative from subgroups IGHV1 and IGHV4 and three representatives from subgroup IGHV3. The VH subgroups are listed in M.-P. Lefranc (2001) "Nomenclature of the Human Immunoglobulin Heavy (IGH) Genes", *Experimental and Clinical Immunogenetics* 18:100-116. The framework sequences of the human germline sequence with the closest match are used to construct a humanized VH domain.

The rodent anti-huGITR antibodies disclosed herein are all of the kappa subclass of VL. The amino acid sequences of the non-human VL domain (e.g. SEQ ID NOs: 12-22) is compared to a group of four human VL kappa germline amino acid sequences. The group of four is comprised of one representative from each of four established human VL subgroups listed in V. Barbie & M.-P. Lefranc (1998) "The Human Immunoglobulin Kappa Variable (IGKV) Genes and Joining (IGKJ) Segments", *Experimental and Clinical Immunogenetics* 15:171-183 and M.-P. Lefranc (2001) "Nomenclature of the Human Immunoglobulin Kappa (IGK) Genes", *Experimental and Clinical Immunogenetics* 18:161-174. The four subgroups also correspond to the four subgroups listed in Kabat et al. (1991-5th Ed.) "Sequences of Proteins of Immunological Interest", U.S. Department of Health and Human Services, NIH Pub. 91-3242, pp. 103-130. The framework sequences of the human germline sequence with the closest match are used to construct a humanized VL domain.

Once the target amino acid sequences of the variable heavy and light chains are determined, plasmids encoding the full-length humanized antibody may be generated. Plasmid sequences may be altered using Kunkel mutagenesis (see, e.g., Kunkel T A. (1985) *Proc. Natl. Acad. Sci.* U.S.A 82:488-492) to change the DNA sequence to the target humanized antibody sequences. Simultaneously, codon optimization may be performed to provide for potentially optimal expression.

Antibodies of the present invention can be humanized using a method that identifies an acceptor germline sequence for a humanized antibody, and comprises the steps of: a) identifying a non-human antibody that has the desired biological activity; b) determining the amino acid sequence of a non-human antibody $V_H$ and $V_L$ domains; and c) comparing the nonhuman antibody sequence to a group of human germline sequences, wherein the comparison comprises the sub-steps of: 1) assigning the non-human V sequences residue numbers according to Kabat supra; 2) delineating the CDR and FR regions in the sequence according to Kabat supra; 3) assigning a predetermined numerical score at specific residue position for which the non-human and human antibody germline sequences are identical; and 4) totaling all of the residue scores to generate a total score for each human germline sequence; and d) identifying the human germline sequence with the highest total residue score as the acceptor germline sequence. In one embodiment, the method further comprises the substeps of: 5) assigning a numerical score of 1 for each FR residue position for which the non-human and human antibody germline sequences are identical that was not scored in substep (3) to germline sequences with identical total residue scores after substep (4); 6) totaling all of the residue scores to generate a total score for each human germline sequence. In a specific embodiment, the non-human antibody is specific for GITR and enhances the biological activity of GITR. Also provided herein is an antibody generated by the above method.

In one embodiment, the GITR antibody is humanized using the following method. First, the non-human $V_L$ and $V_H$ domains of the GITR antibody are cloned and sequenced, and the amino acid sequence determined. Then, the non-human $V_H$ sequence are compared to a group of three human $V_H$ germline amino acid sequences. The three groups contain one representative from each of subgroups IGHV1, IGHV3 and IGHV4. The $V_H$ subgroups are listed in M.-P. Lefranc, *Exp. Clin. Immunogenetics*, 18:100-116 (2001). Specifically, the comparison with the three germline sequences begins with the assignment of residue numbers to the non-human $V_H$ sequence according to the Kabat numbering system. See Kabat, et al., U.S. Department of Health and Human Services, NIH Pub. 91-3242 (5th Ed., 1991). The non-human $V_H$ sequence are then aligned with each of the three human germline sequences. Since the V genes only comprise $V_H$ residues 1-94, only these residues are considered in the alignment. Next, the complementarity-determining (CDR) and framework (FR) regions in the sequence are delineated. CDR and FR are delineated according to the combination of the definitions provided in Kabat, et al., U.S. Department of Health and Human Services, NIH Pub. 91-3242 (5th Ed., 1991), and C. Chothia & A. M. Lesk, *J. Mol. Biol.*, 196:901-917 (1987). Therefore, the CDR definition used is residues 26-35 for CDR1, residues 50-65 for CDR2, and CDR3 is residues 95-102 for CDR3 of the $V_H$ domain. The next step involves assigning a numerical score at identified residue position where the non-human and human sequences are identical. One example of this scoring is shown in Table 4 below.

TABLE 4

| Residue # | Score | Reason |
|---|---|---|
| 24 | 3 | Affects CDR-H1 |
| 27 | 4 | Affects CDR-H1, 3* |
| 29 | 4 | Affects CDR-H1* |
| 34 | 4 | Affects CDR-H1* |
| 35 | 2 | VH/VL interface |
| 37 | 2 | VH/VL interface |
| 48 | 3 | Affects CDR-H2 |
| 49 | 3 | Affects CDR-H2 |
| 50 | 2 | VH/VL interface |
| 58 | 2 | VH/VL interface |
| 60 | 2 | VH/VL interface |
| 63 | 3 | Affects CDR-H2 |
| 67 | 3 | Affects CDR-H2 |
| 69 | 3 | Affects CDR-H2 |
| 71 | 4 | Affects CDR-H2* |
| 73 | 3 | Affects CDR-H1 |
| 76 | 3 | Affects CDR-H1 |
| 78 | 3 | Affects CDR-H1 |
| 94 | 4 | Affects CDR-H3* |
| max | 57 | |

*Noted as affecting CDR conformation in C. Chothia et al., Nature 342: 877-883, (1989).

After the residue positions are assigned a numerical score, all of the residue scores are totaled. The acceptor germline sequence is the one with the highest total score. In a case where two or more germline sequences have identical scores, then add 1 to the total for each position where the non-human and human sequences are IDENTICAL for the following FR residues: 1-23, 25, 36, 38-47, 66, 68, 70, 72, 74, 75, 77, and 79-93 (max 60). The residue scores are totaled again, and the acceptor germline sequence is the one with the highest total score. If two or more germline sequences still have identical scores, either one can be used as the acceptor germline sequence.

If the $V_L$ sequence is a member of the kappa subclass of $V_L$, the non-human $V_L$ sequence from the GITR specific antibody is compared to a group of four human $V_L$ kappa germline amino acid sequences. The four sequences are comprised of one representative from each of four established human $V_L$ subgroups listed in V. Barbie & M.-P. Lefranc, Exp. Clin. Immunogenetics 15:171-183 (1998) and M.-P. Lefranc, Exp. Clin. Immunogenetics 18:161-174 (2001). The four sequences also correspond to the four subgroups listed in Kabat et al., U.S. Department of Health and Human Services, NIH Pub. 91-3242, pp. 103-130 (5th Ed., 1991). The comparison of the non-human sequence to the four germline sequences begins with the assignment of residue numbers to the non-human $V_L$ sequence residues according to Kabat et al., U.S. Department of Health and Human Services, NIH Pub. 91-3242 (5th Ed., 1991). The non-human $V_L$ sequences are then aligned with each of the four human germline sequences. Since the V genes only comprise $V_L$ residues 1-95, only these residues are considered in the alignment. Next, the complementarity-determining (CDR) and framework (FR) regions are delineated in the sequence. CDR and FR are delineated according to the combination of the definitions provided in Kabat et al., U.S. Department of Health and Human Services, NIH Pub. 91-3242 (5th Ed. 1991), and C. Chothia & A. M. Lesk, J. Mol. Biol., 196:901-917 (1987). Therefore, the CDR definition used is residues 24-34 for CDR1, residues 50-56 for CDR2, and residues 89-97 for CDR3 of the $V_L$ domain. The next step involves assigning a numerical score at identified residue position where the non-human and human sequences are identical. One example of this scoring is shown in Table 5 below.

TABLE 5

| Residue # | Score | Reason |
|---|---|---|
| 2 | 4 | Affects CDR-L1, 3* |
| 25 | 4 | Affects CDR-L1* |
| 29 | 4 | Affects CDR-L1, 3* |
| 34 | 2 | VL/VH interface |
| 43 | 2 | VL/VH interface |
| 55 | 2 | VL/VH interface |
| 58 | 3 | Affects CDR-L2 |
| 89 | 2 | VL/VH interface |
| 91 | 2 | VL/VH interface |
| 94 | 2 | VL/VH interface |
| max | 27 | |

*Noted as affecting CDR conformation in C. Chothia et al., Nature 342: 877-883, (1989).

After the residue positions are assigned a numerical score, all of the residue scores are totaled. The acceptor germline sequence is the one with the highest total score. In a case where two or more germline sequences have identical scores, then add 1 to the total for each position where the non-human and human sequences are IDENTICAL for the following FR residues: 1-3, 5-23, 35-42, 44-49, 57, 59-88 (max 67). The residue scores are totaled again, and the acceptor germline sequence is the one with the highest total score. If two or more germline sequences still have identical scores, either one can be used as the acceptor germline sequence.

The above parental monoclonal antibodies were humanized using this method. SEQ ID NOs: 90, 92, 94, 96, 98, 100, 102, 104, 106, 108, and 110 are the sequences of variable heavy chains polypeptides, and SEQ ID NOs: 91, 93, 95, 97, 99, 101, 103, 105, 107, 109, and 111 are the sequences of the variable light chains.

Example 3

Determining the Equilibrium Dissociation Constant ($K_d$) for Anti-Human GITR Antibodies Using KinExA Technology The equilibrium dissociation constants ($K_d$) for anti human GITR antibodies are determined using the KinExA 3000 instrument. Sapidyne Instruments Inc., Boise Id., USA. KinExA uses the principle of the Kinetic Exclusion Assay method based on measuring the concentration of uncomplexed antibody in a mixture of antibody, antigen and antibody-antigen complex. The concentration of free antibody is measured by exposing the mixture to a solid-phase immobilized antigen for a very brief period of time. In practice, this is accomplished by flowing the solution phase antigen-antibody mixture past antigen-coated particles trapped in a flow cell. Data generated by the instrument are analyzed using custom software. Equilibrium constants are calculated using a mathematical theory based on the following assumptions:

1. The binding follows the reversible binding equation for equilibrium:

$$k_{on}[Ab][Ag] = k_{off}[AbAg]$$

2. Antibody and antigen bind 1:1 and total antibody equals antigen-antibody complex plus free antibody.

3. Instrument signal is linearly related to free antibody concentration.

PMMA particles (Sapidyne, Cat No. 440198) are coated with biotinylated GITR (or a fragment thereof, such as the extracellular domain) according to Sapidyne "Protocol for coating PMMA particles with biotinylated ligands having short or nonexistent linker arms." EZ-LINK™ TFP PEO-biotin (Pierce, Cat. No. 21219) is used for biotinylation of GITR, as per the manufacturer's recommendations (Pierce bulletin 0874).

Example 4

Determining the Equilibrium Dissociation Constant ($K_d$) for Humanized Anti-Human GITR Antibodies Using Biacore Technology BIAcore determinations are performed essentially as described at Example 4 of co-pending, commonly assigned U.S. patent application Ser. No. 11/511,635 (filed 29 Aug. 2006). Briefly, binding partners are immobilized on a BIAcore CM5 sensor chip using standard amine-coupling procedure. Kinetic constants for the various interactions are determined using BIAevaluation software 3.1. The $K_d$ is determined using the calculated dissociation and association rate constants.

GITR antibodies 36E5, 3D6, 61G6, 6H6, 61F6, 1D8, 17F10, 35D8, 49A1, 9E5, and 31H6 had the following Kd values:

TABLE 6

Affinity measurements of GITR antibodies

| Analyte (mAb) | Capture antigen | Ka (1/Ms) (×10$^5$) | Kd (1/s) (×10$^{-6}$) | Apparent Kd (pM) |
|---|---|---|---|---|
| 36E5 | hGITR-hIgG | 8.64 | 177 | 205 |
| 61F6 | hGITR-hIgG | 11.1 | 13530 | 12189 |

TABLE 6-continued

Affinity measurements of GITR antibodies

| Analyte (mAb) | Capture antigen | Ka (1/Ms) (×10$^5$) | Kd (1/s) (×10$^{-6}$) | Apparent Kd (pM) |
|---|---|---|---|---|
| 61G6 | hGITR-hIgG | 0.04 | 69 | 15602 |
| 3D6 | hGITR-hIgG | 0.95 | 766 | 8046 |
| 6H6 | hGITR-hIgG | 6.10 | 919 | 1507 |
| 1D8 | hGITR-hIgG | 4.28 | 196 | 458 |
| 17F10 | hGITR-hIgG | 13.1 | 146 | 111 |
| 35D8 | hGITR-hIgG | 8.01 | 200 | 250 |
| 49A1 | hGITR-hIgG | 4078 | 318 | 665 |
| 9E5 | hGITR-hIgG | 23.3 | 27 | 12 |
| 31H6 | hGITR-hIgG | 15.7 | 7 | ≤5 |

Example 5

Bioassays for the Assessment of Activating Anti-GITR Antibodies

The ability of a monoclonal antibody to biologically enhance GITR activity was assessed by the effect on proliferation of naïve T cells (see, e.g., Ito et al., (2006) PNAS 103(35):13138-43. Naïve CD4' T cells were isolated from peripheral blood mononuclear cells (PBMC) by Ficoll centrifugation followed by using a naïve CD4 T cell isolation kit from STEMCELL Technologies.

In 96-well tissue flat-bottom culture plates, a total of 2×10$^4$ freshly purified naïve CD4 T cells were co-cultured with irradiated CD32-expressing L cells in the presence of an anti-hGITR antibody or the isotype control, which had been pre-coated with anti-CD3.

Tables 7A and 7B shows the effect of varying doses of anti-GITR antibodies on proliferation of naïve CD4+ T cells (KM4-R63 is an isotype control antibody).

TABLE 7A

| Ab conc | 36E5.A5 | | JL5.3D6 | | 61G6.B6 | | 6H6.C3 | | 61F6.B9 | | KM4.R63 | |
|---|---|---|---|---|---|---|---|---|---|---|---|---|
| (ng/mL) | mean | SD | mean | SD | mean | SD | mean | SD | mean | SD | mean | SD |
| 10000 | 83784 | 5854 | 96205 | 9562 | 135047 | 7362 | 91873 | 4218 | 93373 | 4099 | 29662 | 7817 |
| 2500 | 71843 | 7556 | 109291 | 21713 | 115725 | 9792 | 107347 | 6049 | 96296 | 1233 | 27007 | 4572 |
| 625 | 82075 | 6760 | 111455 | 5596 | 75125 | 5258 | 120374 | 10489 | 105194 | 5043 | 25503 | 4699 |
| 156 | 97139 | 11937 | 108929 | 5934 | 45588 | 6309 | 122653 | 7164 | 107643 | 8700 | 27496 | 4019 |
| 39.1 | 90331 | 6422 | 124377 | 26014 | 40075 | 2611 | 103621 | 2111 | 107473 | 2179 | 25650 | 197 |
| 9.8 | 78668 | 11867 | 79317 | 2260 | 34335 | 3038 | 59965 | 4439 | 96267 | 10551 | 24722 | 3890 |
| 2.4 | 47467 | 9197 | 43088 | 1264 | 28872 | 2754 | 35629 | 3144 | 61257 | 3294 | 24851 | 1945 |
| 0.61 | 31043 | 6389 | 33847 | 1985 | 32642 | 3155 | 30245 | 12806 | 37587 | 1858 | 29232 | 7135 |
| 0.15 | 26240 | 8161 | 30774 | 7303 | 35642 | 4447 | 33443 | 8983 | 31955 | 2689 | 26627 | 1010 |
| 0.04 | 27502 | 4280 | 33342 | 3656 | 30969 | 1537 | 38543 | 8259 | 34931 | 5787 | 31039 | 3042 |

TABLE 7B

| Ab conc | 1D8.B5 | | 35D8.B10 | | 49A1.B1 | | 9E5.C1 | | 31H6.B7 | | 17F10.B1 | |
|---|---|---|---|---|---|---|---|---|---|---|---|---|
| (ng/mL) | mean | SD | mean | SD | mean | SD | mean | SD | mean | SD | mean | SD |
| 1000.0 | — | — | 97278 | 3127 | 78031 | 5394 | 83553 | 6596 | 87531 | 1051 | 89358 | 12570 |
| 416.7 | — | — | 89761 | 9163 | 86306 | 3807 | 79685 | 7730 | 86915 | 2652 | 85702 | 9724 |
| 173.6 | 90962 | 3417 | 96241 | 3423 | 93594 | 4229 | 84579 | 5929 | 96935 | 4442 | 87519 | 7556 |
| 72.3 | 102810 | 3353 | 92371 | 5048 | 96126 | 5395 | 85291 | 16030 | 98595 | 7374 | 83511 | 5009 |
| 30.1 | 112003 | 5405 | 95258 | 8152 | 95517 | 6187 | 83407 | 5503 | 94683 | 7610 | 86986 | 2717 |
| 12.6 | 115163 | 6429 | 86232 | 5329 | 86001 | 1893 | 85659 | 5087 | 90531 | 3957 | 90231 | 2079 |
| 5.2 | 98161 | 5423 | 71405 | 10471 | 72192 | 1776 | 77653 | 5524 | 79605 | 7438 | 77786 | 5065 |
| 2.2 | 78492 | 1831 | 59817 | 745 | 61053 | 239 | 69187 | 7450 | 67645 | 1972 | 73420 | 12592 |
| 0.9 | 64788 | 773 | 50713 | 2257 | 54096 | 2816 | 60922 | 7139 | 56972 | 4470 | 61950 | 4598 |
| 0.4 | 60794 | 5069 | 52287 | 5015 | 54348 | 1018 | 60105 | 6687 | 58490 | 582 | 58704 | 7820 |

Example 5

Treatment of Tumors with TGF-β and GITR Antibodies

Previous studies revealed that gene expression of 4T1 tumors had increased levels of TGF-β mRNA. It was hypothesized that immune co-stimulation by anti-GITR agonist combined with removal of immune suppression by inhibition of TGF-β signaling would induce synergistic anti-tumor efficacy.

To test this hypothesis, $1.5 \times 10^5$ 4T1 tumor cells were implanted subcutaneously at the right flank of Balb/C mice. Four or seven days after tumor implantation, a neutralization antibody to murine TGF-β (1D11; Bioexpress) was injected at 100 μgs/200 μL subcutaneously at the neck and repeated every three days for a total of 7 doses. Anti-mouse GITR agonist antibody, DTA-1, was injected at day 7, 14, and 21 at 500 μg/200 μL. Tumor volume was measured every three days. As shown in Table 8 below, DTA-1 or anti-TGF-β alone has little effect by themselves. Combined treatment induces synergistic effect on either of the starting days of anti-TGF-β treatment (day 4 or day 7 post tumor implantation). Values are tumor volume ($mm^3$).

TABLE 8

Anti-tumor efficacy by anti-mGITR and/or anti-TGF-β

| Post tumor Imp | IgG2b | | | DTA1 | | | anti-TG-β(D7) | | |
|---|---|---|---|---|---|---|---|---|---|
| | MEAN | SD | N | MEAN | SD | N | MEAN | SD | N |
| Day 7  | 57.476  | 4.383 | 12 | 55.4614 | 5.28  | 12 | 55.7903 | 6.85  | 12 |
| Day 11 | 160.904 | 11.87 | 12 | 131.563 | 10.67 | 12 | 141.827 | 14.94 | 12 |
| Day 14 | 259.459 | 10.42 | 12 | 213.981 | 20.49 | 12 | 222.383 | 18.47 | 12 |
| Day 18 | 408.553 | 24.34 | 12 | 340.876 | 21.30 | 12 | 309.058 | 24.45 | 12 |
| Day 21 | 627.802 | 34.23 | 12 | 519.613 | 29.11 | 12 | 524.622 | 44.18 | 12 |
| Day 25 | 810.945 | 41.97 | 12 | 761.875 | 45.07 | 12 | 699.235 | 47.79 | 12 |
| Day 29 | 1099.43 | 33.47 | 12 | 1006.18 | 39.89 | 12 | 908.552 | 32.36 | 12 |

| Post tumor Imp | DTA1 + anti-TGF-β(D7) | | | anti-TGF-β(D4) | | | DTA1 + anti-TGF-β(D4) | | |
|---|---|---|---|---|---|---|---|---|---|
| | MEAN | SD | N | MEAN | SD | N | MEAN | SD | N |
| Day 7  | 49.1208 | 4.24  | 12 | 54.551  | 6.01  | 10 | 48.432  | 6.80  | 10 |
| Day 11 | 67.9306 | 5.98  | 12 | 140.118 | 15.54 | 10 | 70.202  | 3.65  | 10 |
| Day 14 | 58.5907 | 5.01  | 12 | 193.78  | 26.52 | 10 | 39.651  | 9.522 | 10 |
| Day 18 | 100.977 | 14.92 | 12 | 315.661 | 42.47 | 10 | 45.928  | 20.59 | 10 |
| Day 21 | 185.615 | 16.66 | 12 | 515.88  | 55.56 | 10 | 92.660  | 45.67 | 10 |
| Day 25 | 336.241 | 27.26 | 12 | 718.21  | 73.21 | 10 | 213.447 | 63.72 | 10 |
| Day 29 | 511.284 | 32.98 | 12 | 956.36  | 83.12 | 10 | 382.504 | 94.91 | 10 |

Example 6

Antibody-Radiation Combined Treatment of CT26 Tumors

CT26 tumor cells ($3 \times 10^5$) were implanted subcutaneously on left flanks of Balb/c mice. Local irradiation (10 Gy) was applied to tumors that grew to 300 $mm^3$, after observing that DTA-1 alone did not have tumor-killing efficacy. A day after the irradiation, DTA-1 (500 ug) was injected subcutaneously on the neck area and repeated every week for a total of three doses. Tumor volume was measured every two to five days. In the group of 10 mice that underwent local irradiation and DTA-1 combined treatment, 5 mice completely rejected the tumors and survived up to 3 months. DTA-1 or irradiation alone did not exhibit tumor rejection (see, e.g., FIG. 1).

Example 7

Epitope Mapping of GITR Antibodies

As noted above, DTA-1 is an agonist antibody raised again mouse GITR (see, e.g., Shimizu, et al. supra). DTA-1 has been shown to have potent anti-tumor activities in mouse models of cancer (see, e.g., Cohen, et al. (2006) *Cancer Res.* 66:4904-4912; Ramirez-Montagut, et al. (2006) *J. Immunol.* 176:6434-6442; Zhou, et al. (2007) *J. Immunol.* 179:7365-7375; and Ko, et al. (2005) *J. Exp. Med.* 202:885-891).

To determine if the antibodies described above bound to a DTA-1-like epitope on the human GITR protein, the DTA-1 epitope was first mapped on the mouse GITR protein. Without a crystal structure of human or mouse GITR available, the DTA-1 epitope was determined using standard site directed mutagenesis techniques (see, e.g., Kunkel (1985) *Proc. Natl. Acad. Sci.* 82:488-492) and the general principles of modularity of the TNF-receptor family (see, e.g., Naismith and Sprang, supra).

Once the mouse GITR epitope recognized by DTA-1 was determined, the corresponding residues on human GITR were changed to the mouse residues thereby conferring DTA-1 binding to human GITR. From this, it was determined the DTA-1-like epitope on human GITR spanned modules 3 and 4 (see FIG. 2), and the human GITR (SEQ ID NO: 89) epitope recognized by two of the above-identified antibodies comprised $Gly^{57}$, $Arg^{65}$, $His^{67}$, $Lys^{80}$, $Phe^{81}$, $Ser^{82}$, and $Gln^{86}$.

Example 8

Treatment of Viral Infections with Anti-GITR Antibodies

HIV infection is characterized by defects in the generation and maintenance of central memory cells. CD8+ central memory cells have a shorter half-life and are less abundant in HIV-infected individuals than in controls. Also, the frequency of both CD4+ and CD8+ HIV-specific T cells decreases rapidly after initiation of highly active antiretroviral therapy (HAART). Co-stimulation on CD4+ by anti-GITR may provide a mechanism to increase memory CD8+ response and to contribute to clearance of the virus. It has been shown that treatment of persistently Friend virus-infected mice with anti-GITR antibody to ameliorate suppression by Tregs significantly improved IFN-γ production by the CD8+ T cells and allowed a significant reduction in viral loads (Dittmer et al., (2004) *Immunity* 20: 293-303).

Another characteristic of HIV infection is massive apoptosis of CD4+ T cells starting early in HIV infection. The progressive apoptotic deletion of CD4 T cells contributes to weakened HIV-specific cellular immune responses and to the development of AIDS. GITR co-stimulation has been shown to enhance murine antigen-specific cytokine secretion by protecting T cells from apoptosis. Lahey et al. (2007) *J Infect Dis.* 196: 43-49) demonstrated that anti-GITR treatment of HIV-specific CD4+ T cells enhances their cytokine expression and protects them from apoptosis.

For infections resulting from viral causes, the antibodies of the invention may be combined by application simultaneous with, prior to or subsequent to application of standard therapies for treating viral infections. Such standard therapies vary depending upon type of virus, although in almost all cases, administration of human serum containing antitibodies (e.g., IgA, IgG) specific to the virus can be effective.

Influenza infection results in fever, cough, myalgia, headache and malaise, which often occur in seasonal epidemics. Influenza is also associated with a number of postinfectious disorders, such as encephalitis, myopericarditis, Goodpasture's syndrome, and Reye's syndrome. Influenza infection also suppresses normal pulmonary antibacterial defenses, such that patient's recovering from influenza have an increased risk of developing bacterial pneumonia.

Influenza viral surface proteins show marked antigenic variation, resulting from mutation and recombination. Thus, cytolytic T lymphocytes are the host's primary vehicle for the elimination of virus after infection. Influenza is classified into three primary types: A, B and C. Influenza A is unique in that it infects both humans and many other animals (e.g., pigs, horses, birds and seals) and is the principal cause of pandemic influenza. Also, when a cell is infected by two different influenza A strains, the segmented RNA genomes of two parental virus types mix during replication to create a hybrid replicant, resulting in new epidemic strains. Influenza B does not replicate in animals and thus has less genetic variation and influenza C has only a single serotype.

Most conventional therapies are palliatives of the symptoms resulting from infection, while the host's immune response actually clears the disease. However, certain strains (e.g., influenza A) can cause more serious illness and death. Influenza A may be treated both clinically and prophylactically by the administration of the cyclic amines inhibitors amantadine and rimantadine, which inhibit viral replication. However, the clinical utility of these drugs is limited due to the relatively high incidence of adverse reactions, their narrow anti-viral spectrum (influenza A only), and the propensity of the virus to become resistant. The administration of serum IgG antibody to the major influenza surface proteins, hemagglutinin and neuraminidase can prevent pulmonary infection, whereas mucosal IgA is required to prevent infection of the upper respiratory tract and trachea. The most effective current treatment for influenza is vaccination with the administration of virus inactivated with formalin or β-propiolactone.

After an incubation of 9-11 days, hosts infected with the measles virus develop fever, cough, coryza and conjunctivitis. Within 1-2 days, an erythematous, maculopapular rash develop, which quickly spreads over the entire body. Because infection also suppresses cellular immunity, the host is at greater risk for developing bacterial superinfections, including otitis media, pneumonia and postinfectious encephalomyelitis. Acute infection is associated with significant morbidity and mortality, especially in malnourished adolescents.

Treatment for measles includes the passive administration of pooled human IgG, which can prevent infection in non-immune subjects, even if given up to one week after exposure.

However, prior immunization with live, attenuated virus is the most effective treatment and prevents disease in more than 95% of those immunized. As there is one serotype of this virus, a single immunization or infection typically results in protection for life from subsequent infection.

In a small proportion of infected hosts, measles can develop into SSPE, which is a chronic progressive neurologic disorder resulting from a persistent infection of the central nervous system. SSPE is caused by clonal variants of measles virus with defects that interfere with virion assembly and budding. For these patients, reactivation of T-cells with the antibodies of the invention so as to facilitate viral clearance would be desirable.

Hepatitis B virus (HB-V) is the most infectious known bloodborne pathogen. It is a major cause of acute and chronic hepatitis and hepatic carcinoma, as well as life-long, chronic infection. Following infection, the virus replicates in hepatocytes, which also then shed the surface antigen HBsAg. The detection of excessive levels of HBsAg in serum is used a standard method for diagnosing a hepatitis B infection. An acute infection may resolve or it can develop into a chronic persistent infection.

Current treatments for chronic HBV include α-interferon, which increases the expression of class I human leukocyte antigen (HLA) on the surface of hepatocytes, thereby facilitating their recognition by cytotoxic T lymphocytes. Additionally, the nucleoside analogs ganciclovir, famciclovir and lamivudine have also shown some efficacy in the treatment of HBV infection in clinical trial. Additional treatments for HBV include pegylated α-interferon, adenfovir, entecavir and telbivudine. While passive immunity can be conferred through parental administration of anti-HBsAg serum antibodies, vaccination with inactivated or recombinant HBsAg also confers resistance to infection. The anti-GITR antibodies of the invention may be combined with conventional treatments for hepatitis B infections for therapeutic advantage.

Hepatitis C virus (HC-V) infection may lead to a chronic form of hepatitis, resulting in cirrosis. While symptoms are similar to infections resulting from Hepatitis B, in distinct contrast to HB-V, infected hosts can be asymptomatic for 10-20 years. Treatment for HC-V infection includes the administration of a combination of α-interferon and ribavirin. A promising potential therapy for HC-V infection is the protease inhibitor telaprevir (VX-960). Additional treatments include: anti-PD-1 antibody (MDX-1106, Medarex), bavituximab (an antibody that binds anionic phospholipid phosphatidylserine in a B2-glycoprotein I dependent manner, Peregrine Pharmaceuticals), anti-HPV viral coat protein E2 antibod(y)(ies) (E.g., ATL 6865–Ab68+Ab65, XTL Pharmaceuticals) and Civacir® (polyclonal anti-HCV human immune globulin). The anti-GITR antibodies of the invention may be combined with one or more of these treatments for hepatitis C infections for therapeutic advantage.

Table 9 provides a brief description of the sequences in the sequence listing.

| SEQ ID NO.: | Description |
|---|---|
| 1 | 36E5 Heavy Chain Variable |
| 2 | 3D6 Heavy Chain Variable |
| 3 | 61G6 Heavy Chain Variable |
| 4 | 6H6 Heavy Chain Variable |
| 5 | 61F6 Heavy Chain Variable |
| 6 | 1D8 Heavy Chain Variable |
| 7 | 17F10 Heavy Chain Variable |
| 8 | 35D8 Heavy Chain Variable |
| 9 | 49A1 Heavy Chain Variable |
| 10 | 9E5 Heavy Chain Variable |
| 11 | 31H6 Heavy Chain Variable |
| 12 | 36E5 Light Chain Variable |
| 13 | 3D6 Light Chain Variable |
| 14 | 61G6 Light Chain Variable |
| 15 | 6H6 Light Chain Variable |
| 16 | 61F6 Light Chain Variable |
| 17 | 1D8 Light Chain Variable |
| 18 | 17F10 Light Chain Variable |
| 19 | 35D8 Light Chain Variable |
| 20 | 49A1 Light Chain Variable |
| 21 | 9E5 Light Chain Variable |
| 22 | 31H6 Light Chain Variable |
| 23 | 36E5 CDRH1 |
| 24 | 3D6 CDRH1 |
| 25 | 61G6 CDRH1 |
| 26 | 6H6 CDRH1 |
| 27 | 61F6 CDRH1 |
| 28 | 1D8 CDRH1 |
| 29 | 17F10 CDRH1 |
| 30 | 35D8 CDRH1 |
| 31 | 49A1 CDRH1 |
| 32 | 9E5 CDRH1 |
| 33 | 31H6 CDRH1 |
| 34 | 36E5 CDRH2 |
| 35 | 3D6 CDRH2 |
| 36 | 61G6 CDRH2 |
| 37 | 6H6 CDRH2 |
| 38 | 61F6 CDRH2 |
| 39 | 1D8 CDRH2 |
| 40 | 17F10 CDRH2 |
| 41 | 35D8 CDRH2 |
| 42 | 49A1 CDRH2 |
| 43 | 9E5 CDRH2 |
| 44 | 31H6 CDRH2 |
| 45 | 36E5 CDRH3 |
| 46 | 3D6 CDRH3 |
| 47 | 61G6 CDRH3 |
| 48 | 6H6 CDRH3 |
| 49 | 61F6 CDRH3 |
| 50 | 1D8 CDRH3 |
| 51 | 17F10 CDRH3 |
| 52 | 35D8 CDRH3 |
| 53 | 49A1 CDRH3 |
| 54 | 9E5 CDRH3 |
| 55 | 31H6 CDRH3 |
| 56 | 36E5 CDRL1 |
| 57 | 3D6 CDRL1 |
| 58 | 61G6 CDRL1 |
| 59 | 6H6 CDRL1 |
| 60 | 61F6 CDRL1 |
| 61 | 1D8 CDRL1 |
| 62 | 17F10 CDR L1 |
| 63 | 35D8 CDR L1 |
| 64 | 49A1 CDR L1 |
| 65 | 9E5 CDR L1 |
| 66 | 31H6 CDR L1 |
| 67 | 36E5 CDRL2 |
| 68 | 3D6 CDRL2 |
| 69 | 61G6 CDRL2 |
| 70 | 6H6 CDRL2 |
| 71 | 61F6 CDRL2 |
| 72 | 1D8 CDRL2 |
| 73 | 17F10 CDR L2 |
| 74 | 35D8 CDR L2 |
| 75 | 49A1 CDR L2 |
| 76 | 9E5 CDR L2 |
| 77 | 31H6 CDR L2 |
| 78 | 36E5 CDRL3 |
| 79 | 3D6 CDRL3 |
| 80 | 61G6 CDRL3 |
| 81 | 6H6 CDRL3 |
| 82 | 61F6 CDRL3 |
| 83 | 1D8 CDRL3 |
| 84 | 17F10 CDR L3 |
| 85 | 35D8 CDR L3 |
| 86 | 49A1 CDR L3 |
| 87 | 9E5 CDR L3 |
| 88 | 31H6 CDR L3 |
| 89 | Human GITR |
| 90 | Humanized 1D8 VH |
| 91 | Humanized 1D8 VL |
| 92 | Humanized 3D6 VH |
| 93 | Humanized 3D6 VL |
| 94 | Humanized 6H6 VH |
| 95 | Humanized 6H6 VL |
| 96 | Humanized 9E5 VH |
| 97 | Humanized 9E5 VL |
| 98 | Humanized 31H6 VH |
| 99 | Humanized 31H6 VL |
| 100 | Humanized 17F10 VH |
| 101 | Humanized 17F10 VL |
| 102 | Humanized 35D8 VH |
| 103 | Humanized 35D8 VL |
| 104 | Humanized 36E5 VH |
| 105 | Humanized 36E5 VL |
| 106 | Humanized 49A1 VH |
| 107 | Humanized 49A1 VL |
| 108 | Humanized 61F6 VH |
| 109 | Humanized 61F6 VL |
| 110 | Humanized 61G6 VH |
| 111 | Humanized 61G6 VL |

What is claimed is:

1. A binding compound that binds to human GITR comprising:
   a) an antibody light chain variable domain, or antigen binding fragment thereof, having three CDR sequences selected from the group consisting of SEQ ID NOs: 56, 67, and 78; and
   b) an antibody heavy chain variable domain, or antigen binding fragment thereof, having three CDR sequences selected from the group consisting of SEQ ID NOs: 23, 34, and 45.

2. A binding compound of claim 1 wherein:
   a) the heavy chain variable domain comprises the amino acid sequence of SEQ ID NO: 104; and
   b) the light chain variable domain comprises the amino acid sequence of SEQ ID NO: 105.

3. The binding compound of claim 2, further comprising a heavy chain constant region comprising a γ1 human heavy chain constant region.

4. The binding compound of claim 2, further comprising a heavy chain constant region comprising a γ4 human heavy chain constant region.

5. The binding compound of claim 2, wherein the binding compound is an antibody fragment selected from the group consisting of Fab, Fab', Fab'-SH, Fv, scFv, F(ab')$_2$, and a diabody.

6. A pharmaceutical composition comprising the antibody binding compound of claim 2 and a pharmaceutically acceptable carrier.

* * * * *

SEQUENCE LISTING

```
<160> NUMBER OF SEQ ID NOS: 111

<210> SEQ ID NO 1
<211> LENGTH: 118
<212> TYPE: PRT
<213> ORGANISM: Mus musculus

<400> SEQUENCE: 1

Glu Val Asn Leu Val Glu Ser Gly Gly Gly Leu Val Lys Pro Gly Gly
1               5                   10                  15

Ser Leu Lys Val Ser Cys Ala Ala Ser Gly Phe Thr Phe Ser Ser Tyr
            20                  25                  30
```

Ala Met Ser Trp Val Arg Gln Thr Pro Glu Lys Arg Leu Glu Trp Val
            35                  40                  45

Ala Ser Ile Ser Ser Gly Gly Thr Thr Tyr Tyr Pro Asp Ser Val Lys
 50                  55                  60

Gly Arg Phe Thr Ile Ser Arg Asp Asn Ala Arg Asn Ile Leu Tyr Leu
 65                  70                  75                  80

Gln Met Ser Ser Leu Arg Ser Glu Asp Thr Ala Met Tyr Tyr Cys Ala
                85                  90                  95

Arg Val Gly Gly Tyr Tyr Asp Ser Met Asp Tyr Trp Gly Gln Gly Ile
            100                 105                 110

Ser Val Thr Asp Ser Ser
            115

<210> SEQ ID NO 2
<211> LENGTH: 123
<212> TYPE: PRT
<213> ORGANISM: Rattus norvegicus

<400> SEQUENCE: 2

Glu Val Gln Leu Val Glu Ser Gly Gly Gly Leu Val Gln Pro Gly Arg
 1               5                  10                  15

Ser Leu Lys Leu Ser Cys Ala Ala Ser Gly Phe Thr Phe Ser Asp Tyr
            20                  25                  30

Tyr Met Ala Trp Val Arg Gln Ala Pro Thr Lys Gly Leu Glu Trp Val
            35                  40                  45

Ala Tyr Ile His Ala Asn Gly Ser Thr Tyr Tyr Arg Asp Ser Val
 50                  55                  60

Arg Gly Arg Phe Ser Ile Ser Arg Asp Asn Gly Lys Ser Thr Leu Tyr
 65                  70                  75                  80

Leu Gln Met Asp Ser Leu Arg Ser Glu Asp Thr Ala Thr Tyr Tyr Cys
                85                  90                  95

Thr Thr Gly Ser Phe Met Tyr Ala Ala Asp Tyr Tyr Ile Met Asp Ala
            100                 105                 110

Trp Gly Gln Gly Ala Ser Val Thr Val Ser Ser
            115                 120

<210> SEQ ID NO 3
<211> LENGTH: 118
<212> TYPE: PRT
<213> ORGANISM: Mus musculus

<400> SEQUENCE: 3

Asp Val Gln Leu Gln Glu Ser Gly Pro Gly Leu Val Lys Pro Ser Gln
 1               5                  10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
            35                  40                  45

Met Gly Tyr Ile Ser Tyr Ser Gly Ser Thr Arg Tyr Asn Pro Ser Leu
 50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Ser Glu Asp Thr Ala Thr Tyr Tyr Cys
                85                  90                  95

Ala Arg Gln Leu Gly Leu Arg Phe Phe Asp Tyr Trp Gly Gln Gly Thr
            100                 105                 110

```
Thr Leu Thr Val Ser Ser
        115

<210> SEQ ID NO 4
<211> LENGTH: 118
<212> TYPE: PRT
<213> ORGANISM: Mus musculus

<400> SEQUENCE: 4

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Arg Tyr
            20                  25                  30

Trp Ile Glu Trp Ile Lys Gln Arg Pro Gly His Gly Leu Glu Trp Ile
        35                  40                  45

Gly Glu Ile Leu Pro Gly Ser Gly Ser Asn Tyr Asn Glu Lys Phe
    50                  55                  60

Lys Asp Lys Ala Thr Phe Thr Ala Asp Thr Ser Ser Asn Thr Ala Tyr
65                  70                  75                  80

Met Gln Phe Ser Ser Leu Thr Ser Glu Asp Ser Ala Val Tyr Tyr Cys
                85                  90                  95

Ala Arg Lys Val Tyr Tyr Ala Met Asp Phe Trp Gly Gln Gly Thr
            100                 105                 110

Ser Val Thr Val Ser Ser
        115

<210> SEQ ID NO 5
<211> LENGTH: 119
<212> TYPE: PRT
<213> ORGANISM: Mus musculus

<400> SEQUENCE: 5

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Arg Ser Val Tyr Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Leu Gly Gly Tyr Tyr Asp Thr Met Asp Tyr Trp Gly Gln Gly
            100                 105                 110

Thr Ser Val Thr Val Ser Ser
        115

<210> SEQ ID NO 6
<211> LENGTH: 122
<212> TYPE: PRT
<213> ORGANISM: Mus musculus

<400> SEQUENCE: 6

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30
```

```
Gly Met Gly Val Gly Trp Ile Arg Gln Pro Ser Gly Lys Gly Leu Glu
            35                  40                  45
Trp Leu Ala His Ile Trp Trp Asp Asp Lys Tyr Tyr Ser Pro Ser
 50                  55                  60
Leu Lys Ser Gln Leu Thr Ile Ser Lys Asp Thr Ser Arg Asn Gln Val
 65                  70                  75                  80
Phe Leu Lys Ile Thr Ser Leu Asp Thr Ala Asp Thr Ala Thr Tyr Tyr
                    85                  90                  95
Cys Val Arg Ser Tyr Tyr Tyr Gly Ser Ser Gly Ala Met Asp Tyr Trp
                    100                 105                 110
Gly Gln Gly Thr Ser Val Thr Val Ser Ser
            115                 120

<210> SEQ ID NO 7
<211> LENGTH: 117
<212> TYPE: PRT
<213> ORGANISM: Mus musculus

<400> SEQUENCE: 7

Glu Val Lys Leu Val Glu Ser Gly Gly Gly Phe Val Lys Pro Gly Gly
 1               5                   10                  15
Ser Leu Lys Leu Ser Cys Ala Ala Ser Gly Phe Thr Val Arg Asn Tyr
                 20                  25                  30
Ala Met Ser Trp Val Arg Gln Thr Pro Glu Lys Arg Leu Glu Trp Val
            35                  40                  45
Ala Ser Ile Ser Thr Gly Asp Arg Ser Tyr Leu Pro Asp Ser Met Lys
 50                  55                  60
Gly Arg Phe Thr Ile Ser Arg Asp Asn Ala Arg Asn Ile Leu Tyr Leu
 65                  70                  75                  80
Gln Met Ser Ser Leu Arg Ser Glu Asp Thr Ala Ile Tyr Tyr Cys Gln
                    85                  90                  95
Arg Tyr Phe Asp Phe Asp Ser Phe Ala Phe Trp Gly Gln Gly Thr Leu
                    100                 105                 110
Val Thr Val Ser Ala
            115

<210> SEQ ID NO 8
<211> LENGTH: 120
<212> TYPE: PRT
<213> ORGANISM: Mus musculus

<400> SEQUENCE: 8

Glu Val Gln Leu Gln Glu Ser Gly Pro Ser Leu Val Lys Pro Ser Gln
 1               5                   10                  15
Thr Leu Ser Leu Thr Cys Ser Val Thr Gly Asp Ser Ile Thr Ser Gly
                 20                  25                  30
Tyr Trp Asn Trp Ile Arg Lys Phe Pro Gly Asn Lys Leu Glu Tyr Met
            35                  40                  45
Gly Tyr Ile Ser Tyr Ser Gly Ser Thr Tyr Tyr Asn Pro Ser Leu Arg
 50                  55                  60
Gly Arg Ile Ser Ile Thr Arg Asp Thr Ser Lys Ser Gln Tyr Tyr Leu
 65                  70                  75                  80
Gln Leu Ser Ser Val Thr Thr Glu Asp Thr Ala Thr Tyr Tyr Cys Ser
                    85                  90                  95
Arg Arg His Leu Gly Ser Gly Tyr Gly Trp Phe Ala Tyr Trp Gly Gln
                    100                 105                 110
```

-continued

```
Gly Thr Leu Val Thr Val Ser Ala
        115                 120

<210> SEQ ID NO 9
<211> LENGTH: 120
<212> TYPE: PRT
<213> ORGANISM: Mus musculus

<400> SEQUENCE: 9

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Lys Phe Glu Tyr Met
        35                  40                  45

Gly Phe Ile Ser Tyr Ser Gly Asn Thr Tyr Tyr Asn Pro Ser Leu Arg
    50                  55                  60

Ser Arg Ile Ser Ile Thr Arg Asp Thr Ser Lys Asn Gln Tyr Phe Leu
65                  70                  75                  80

His Leu Asn Ser Val Thr Thr Glu Asp Thr Ala Thr Tyr Tyr Cys Ser
                85                  90                  95

Arg Arg His Leu Ile Ser Gly Tyr Gly Trp Phe Ala Tyr Trp Gly Gln
            100                 105                 110

Gly Thr Leu Val Thr Val Ser Ala
        115                 120

<210> SEQ ID NO 10
<211> LENGTH: 121
<212> TYPE: PRT
<213> ORGANISM: Rattus norvegicus

<400> SEQUENCE: 10

Gln Val Thr Leu Lys Glu Ser Gly Pro Gly Ile Leu Gln Pro Ser Gln
1               5                   10                  15

Thr Leu Ser Leu Thr Cys Thr Phe Ser Gly Phe Ser Leu Ser Thr Tyr
            20                  25                  30

Gly Val Gly Val Gly Trp Ile Arg Gln Pro Ser Gly Lys Gly Leu Glu
        35                  40                  45

Trp Leu Ala Asn Ile Trp Trp Asp Asp Asp Asn Tyr Tyr Asn Pro Ser
    50                  55                  60

Leu Ile His Arg Leu Thr Val Ser Lys Asp Thr Ser Asn Asn Gln Ala
65                  70                  75                  80

Phe Leu Lys Ile Thr Asn Val Asp Thr Ala Glu Thr Ala Thr Tyr Tyr
                85                  90                  95

Cys Ala Gln Ile Lys Glu Pro Arg Asp Trp Phe Phe Glu Phe Trp Gly
            100                 105                 110

Pro Gly Thr Met Val Ser Val Ser Ser
        115                 120

<210> SEQ ID NO 11
<211> LENGTH: 121
<212> TYPE: PRT
<213> ORGANISM: Rattus norvegicus

<400> SEQUENCE: 11

Gln Val Thr Leu Lys Glu Ser Gly Pro Gly Ile Leu Gln Pro Ser Gln
1               5                   10                  15

Thr Leu Ser Leu Thr Cys Thr Phe Ser Gly Phe Ser Leu Ser Thr Tyr
            20                  25                  30
```

```
Gly Val Gly Val Gly Trp Ile Arg Gln Pro Ser Gly Lys Gly Leu Glu
            35                  40                  45

Trp Leu Ala Asn Ile Trp Trp Asp Asp Lys Tyr Tyr Asn Pro Ser
 50                  55                  60

Leu Lys Asn Arg Leu Thr Ile Ser Lys Asp Thr Ser Asn Asn Gln Ala
 65                  70                  75                  80

Phe Leu Lys Ile Thr Asn Val Asp Thr Ala Glu Thr Ala Thr Tyr Tyr
                     85                  90                  95

Cys Ala Gln Ile Lys Glu Pro Arg Asp Trp Phe Phe Glu Phe Trp Gly
                    100                 105                 110

Pro Gly Thr Met Val Ser Val Ser Ser
                    115                 120
```

```
<210> SEQ ID NO 12
<211> LENGTH: 113
<212> TYPE: PRT
<213> ORGANISM: Mus musculus

<400> SEQUENCE: 12

Asp Ile Val Leu Thr Gln Ser Pro Ala Ser Leu Ala Val Ser Leu Gly
 1                5                  10                  15

Gln Arg Ala Thr Ile Ser Cys Arg Ala Ser Glu Ser Val Asp Asn Tyr
                20                  25                  30

Gly Val Ser Phe Met Asn Trp Phe Gln Gln Lys Pro Gly Gln Pro Pro
             35                  40                  45

Lys Leu Leu Ile Tyr Ala Ala Ser Asn Gln Gly Ser Gly Val Pro Ala
 50                  55                  60

Arg Phe Ser Gly Ser Gly Ser Gly Thr Asp Phe Ser Leu Asn Ile His
 65                  70                  75                  80

Pro Met Glu Glu Asp Asp Thr Ala Met Tyr Phe Cys Gln Gln Thr Lys
                     85                  90                  95

Glu Val Thr Trp Thr Phe Gly Gly Gly Thr Lys Leu Glu Ile Lys Arg
                    100                 105                 110

Ala
```

```
<210> SEQ ID NO 13
<211> LENGTH: 113
<212> TYPE: PRT
<213> ORGANISM: Rattus norvegicus

<400> SEQUENCE: 13

Asp Val Val Met Thr Gln Thr Pro Val Ser Leu Ser Val Ser Leu Gly
 1                5                  10                  15

Asn Gln Ala Ser Ile Ser Cys Arg Ser Ser Gln Ser Leu Leu His Ser
                20                  25                  30

Asp Gly Asn Thr Phe Leu Ser Trp Tyr Phe Gln Lys Pro Gly Gln Ser
             35                  40                  45

Pro Gln Leu Leu Ile Tyr Leu Ala Ser Asn Arg Phe Ser Gly Val Ser
 50                  55                  60

Asn Arg Phe Ser Gly Ser Gly Ser Gly Thr Asp Phe Thr Leu Lys Ile
 65                  70                  75                  80

Ser Arg Val Glu Pro Glu Asp Leu Gly Val Tyr Tyr Cys Phe Gln His
                     85                  90                  95

Thr His Leu Pro Leu Thr Phe Gly Ser Gly Thr Lys Leu Glu Ile Lys
                    100                 105                 110

Arg
```

<210> SEQ ID NO 14
<211> LENGTH: 108
<212> TYPE: PRT
<213> ORGANISM: Mus musculus

<400> SEQUENCE: 14

Gln Ile Val Leu Thr Gln Ser Pro Ala Leu Met Ser Ala Ser Pro Gly
1               5                   10                  15

Glu Lys Val Thr Met Thr Cys Ser Ala Asn Ser Thr Val Asn Tyr Met
            20                  25                  30

Tyr Trp Tyr Gln Gln Lys Pro Arg Ser Ser Pro Lys Pro Cys Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Asn Ser Asn Pro Pro Thr
                85                  90                  95

Phe Gly Ala Gly Thr Lys Leu Glu Leu Arg Arg Ala
            100                 105

<210> SEQ ID NO 15
<211> LENGTH: 110
<212> TYPE: PRT
<213> ORGANISM: Mus musculus

<400> SEQUENCE: 15

Gln Ile Val Leu Thr Gln Ser Pro Ala Ile Met Ser Val Ser Leu Gly
1               5                   10                  15

Glu Arg Val Thr Val Thr Cys Thr Ala Ser Ser Ser Val Ser Ser Ser
            20                  25                  30

Tyr Phe His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Thr Met Glu
65                  70                  75                  80

Ala Glu Asp Ala Ala Thr Tyr Tyr Cys His Gln Tyr His Arg Ser Pro
                85                  90                  95

Arg Thr Phe Gly Gly Gly Thr Lys Leu Glu Ile Lys Arg Ala
            100                 105                 110

<210> SEQ ID NO 16
<211> LENGTH: 113
<212> TYPE: PRT
<213> ORGANISM: Mus musculus

<400> SEQUENCE: 16

Asp Ile Val Val Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His

```
                65                  70                  75                  80
Pro Met Glu Glu Asp Asp Thr Ala Val Tyr Phe Cys Gln Gln Ser Lys
                    85                  90                  95
Glu Val Pro Phe Thr Phe Gly Ser Gly Thr Lys Leu Glu Ile Lys Arg
                100                 105                 110
Ala

<210> SEQ ID NO 17
<211> LENGTH: 118
<212> TYPE: PRT
<213> ORGANISM: Mus musculus

<400> SEQUENCE: 17

Asp Ile Val Met Thr Gln Thr Pro Leu Ser Leu Pro Val Ser Leu Gly
1               5                   10                  15
Asp Gln Ala Ser Ile Ser Cys Arg Ser Ser Gln Ser Leu Val His Ser
                20                  25                  30
Asp Gly Asn Thr Tyr Leu His Trp Tyr Leu Gln Lys Pro Gly Gln Ser
            35                  40                  45
Pro Lys Leu Leu Ile Tyr Lys Val Ser Lys Arg Phe Ser Gly Val Pro
        50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Phe Cys Ser Gln Ser
                85                  90                  95
Thr His Val Pro Pro Thr Phe Gly Gly Gly Thr Lys Leu Glu Ile Lys
                100                 105                 110
Arg Ala Asp Ala Ala Pro
            115

<210> SEQ ID NO 18
<211> LENGTH: 113
<212> TYPE: PRT
<213> ORGANISM: Mus musculus

<400> SEQUENCE: 18

Asp Ile Gln Met Thr Gln Thr Pro Ser Ser Leu Ser Ala Ser Leu Gly
1               5                   10                  15
Asp Arg Val Thr Ile Ser Cys Arg Ala Ser Gln Asp Ile Asn Asn Phe
                20                  25                  30
Leu Asn Trp Tyr Gln Gln Lys Pro Asp Gly Ser Leu Lys Leu Leu Ile
            35                  40                  45
Tyr Tyr Thr Ser Lys Leu His Ser Gly Val Pro Ser Arg Phe Ser Gly
        50                  55                  60
Ser Gly Ser Gly Thr Asp Phe Ser Leu Thr Ile Ser Asn Leu Asp Gln
65                  70                  75                  80
Glu Asp Val Ala Thr Tyr Phe Cys Gln Gln Gly His Thr Leu Pro Pro
                85                  90                  95
Thr Phe Gly Gly Gly Thr Lys Leu Glu Val Lys Arg Ala Asp Ala Ala
                100                 105                 110
Pro

<210> SEQ ID NO 19
<211> LENGTH: 114
<212> TYPE: PRT
<213> ORGANISM: Mus musculus

<400> SEQUENCE: 19
```

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
    50                  55                  60

Ser Gly Ser Gly Thr Asp Tyr Ala Leu Thr Ile Asn Ser Val Gln Ala
65                  70                  75                  80

Glu Asp Leu Ala Leu Tyr Tyr Cys Gln Gln His Ser Tyr Thr Pro Pro
                85                  90                  95

Trp Thr Phe Gly Gly Gly Thr Lys Leu Glu Ile Arg Arg Ala Asp Ala
            100                 105                 110

Ala Pro

<210> SEQ ID NO 20
<211> LENGTH: 114
<212> TYPE: PRT
<213> ORGANISM: Mus musculus

<400> SEQUENCE: 20

Val Ile Val Met Thr Gln Ser His Lys Phe Met Ser Thr Ser Ile Gly
1               5                   10                  15

Asp Arg Val Asn Ile Thr Cys Lys Ala Ser Gln Asp Val Ile Ser Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Asn Ser Val Gln Ala
65                  70                  75                  80

Glu Asp Arg Ala Leu Tyr Tyr Cys Gln Gln His Ser Tyr Thr Pro Pro
                85                  90                  95

Trp Thr Phe Gly Gly Gly Thr Asn Leu Glu Ile Lys Arg Ala Asp Ala
            100                 105                 110

Ala Pro

<210> SEQ ID NO 21
<211> LENGTH: 113
<212> TYPE: PRT
<213> ORGANISM: Rattus norvegicus

<400> SEQUENCE: 21

Asp Ile Gln Met Thr Gln Thr Pro Ser Ser Met Pro Ala Ser Leu Gly
1               5                   10                  15

Glu Arg Val Thr Ile Phe Cys Arg Ala Ser Gln Gly Val Asn Asn Phe
                20                  25                  30

Leu Thr Trp Tyr Gln Gln Lys Pro Asp Gly Thr Ile Lys Pro Leu Ile
            35                  40                  45

Phe Tyr Thr Ser Asn Leu Gln Ser Gly Val Pro Ser Arg Phe Ser Gly
    50                  55                  60

Ser Gly Ser Gly Thr Asp Tyr Ser Leu Ser Ile Ser Ser Leu Glu Pro
65                  70                  75                  80

Glu Asp Phe Ala Met Tyr Tyr Cys Gln Gln Tyr His Gly Phe Pro Asn
                85                  90                  95

```
Thr Phe Gly Ala Gly Thr Lys Leu Glu Leu Lys Arg Ala Asp Ala Ala
                100                 105                 110
Pro

<210> SEQ ID NO 22
<211> LENGTH: 113
<212> TYPE: PRT
<213> ORGANISM: Rattus norvegicus

<400> SEQUENCE: 22

Asp Ile Gln Met Thr Gln Thr Pro Ser Ser Met Pro Ala Ser Leu Gly
1               5                   10                  15

Glu Arg Val Thr Ile Phe Cys Arg Ala Ser Gln Gly Val Asn Asn Tyr
            20                  25                  30

Leu Thr Trp Tyr Gln Gln Lys Pro Asp Gly Thr Ile Lys Pro Leu Ile
        35                  40                  45

Phe Tyr Thr Ser Asn Leu Gln Ser Gly Val Pro Ser Arg Phe Ser Gly
    50                  55                  60

Ser Gly Ser Gly Thr Asp Tyr Ser Leu Ser Ile Ser Ser Leu Glu Pro
65                  70                  75                  80

Glu Asp Phe Ala Met Tyr Tyr Cys Gln Gln Tyr His Gly Phe Pro Asn
                85                  90                  95

Thr Phe Gly Ala Gly Thr Lys Leu Glu Leu Lys Arg Ala Asp Ala Ala
                100                 105                 110

Pro

<210> SEQ ID NO 23
<211> LENGTH: 10
<212> TYPE: PRT
<213> ORGANISM: Mus musculus

<400> SEQUENCE: 23

Gly Phe Thr Phe Ser Ser Tyr Ala Met Ser
1               5                   10

<210> SEQ ID NO 24
<211> LENGTH: 10
<212> TYPE: PRT
<213> ORGANISM: Rattus norvegicus

<400> SEQUENCE: 24

Gly Phe Thr Phe Ser Asp Tyr Tyr Met Ala
1               5                   10

<210> SEQ ID NO 25
<211> LENGTH: 11
<212> TYPE: PRT
<213> ORGANISM: Mus musculus

<400> SEQUENCE: 25

Gly Tyr Ser Ile Thr Ser Asp Tyr Ala Trp Asn
1               5                   10

<210> SEQ ID NO 26
<211> LENGTH: 10
<212> TYPE: PRT
<213> ORGANISM: Mus musculus

<400> SEQUENCE: 26

Gly Tyr Thr Phe Ser Arg Tyr Trp Ile Glu
1               5                   10
```

```
<210> SEQ ID NO 27
<211> LENGTH: 10
<212> TYPE: PRT
<213> ORGANISM: Mus musculus

<400> SEQUENCE: 27

Gly Tyr Thr Phe Thr Ser Tyr Thr Met His
1               5                   10

<210> SEQ ID NO 28
<211> LENGTH: 12
<212> TYPE: PRT
<213> ORGANISM: Mus musculus

<400> SEQUENCE: 28

Gly Phe Ser Leu Ser Thr Ser Gly Met Gly Val Gly
1               5                   10

<210> SEQ ID NO 29
<211> LENGTH: 10
<212> TYPE: PRT
<213> ORGANISM: Mus musculus

<400> SEQUENCE: 29

Gly Phe Thr Val Arg Asn Tyr Ala Met Ser
1               5                   10

<210> SEQ ID NO 30
<211> LENGTH: 10
<212> TYPE: PRT
<213> ORGANISM: Mus musculus

<400> SEQUENCE: 30

Gly Asp Ser Ile Thr Ser Gly Tyr Trp Asn
1               5                   10

<210> SEQ ID NO 31
<211> LENGTH: 10
<212> TYPE: PRT
<213> ORGANISM: Mus musculus

<400> SEQUENCE: 31

Gly Asp Ser Ile Thr Ser Gly Tyr Trp Asn
1               5                   10

<210> SEQ ID NO 32
<211> LENGTH: 12
<212> TYPE: PRT
<213> ORGANISM: Rattus norvegicus

<400> SEQUENCE: 32

Gly Phe Ser Leu Ser Thr Tyr Gly Val Gly Val Gly
1               5                   10

<210> SEQ ID NO 33
<211> LENGTH: 12
<212> TYPE: PRT
<213> ORGANISM: Rattus norvegicus

<400> SEQUENCE: 33

Gly Phe Ser Leu Ser Thr Tyr Gly Val Gly Val Gly
1               5                   10

<210> SEQ ID NO 34
```

```
<211> LENGTH: 16
<212> TYPE: PRT
<213> ORGANISM: Mus musculus

<400> SEQUENCE: 34

Ser Ile Ser Ser Gly Gly Thr Thr Tyr Tyr Pro Asp Ser Val Lys Gly
1               5                   10                  15

<210> SEQ ID NO 35
<211> LENGTH: 17
<212> TYPE: PRT
<213> ORGANISM: Rattus norvegicus

<400> SEQUENCE: 35

Tyr Ile His Ala Asn Gly Gly Ser Thr Tyr Tyr Arg Asp Ser Val Arg
1               5                   10                  15

Gly

<210> SEQ ID NO 36
<211> LENGTH: 16
<212> TYPE: PRT
<213> ORGANISM: Mus musculus

<400> SEQUENCE: 36

Tyr Ile Ser Tyr Ser Gly Ser Thr Arg Tyr Asn Pro Ser Leu Lys Ser
1               5                   10                  15

<210> SEQ ID NO 37
<211> LENGTH: 17
<212> TYPE: PRT
<213> ORGANISM: Mus musculus

<400> SEQUENCE: 37

Glu Ile Leu Pro Gly Ser Gly Ser Ser Asn Tyr Asn Glu Lys Phe Lys
1               5                   10                  15

Asp

<210> SEQ ID NO 38
<211> LENGTH: 17
<212> TYPE: PRT
<213> ORGANISM: Mus musculus

<400> SEQUENCE: 38

Tyr Ile Asn Pro Arg Ser Val Thr Asn Tyr Asn Gln Lys Phe Lys
1               5                   10                  15

Asp

<210> SEQ ID NO 39
<211> LENGTH: 16
<212> TYPE: PRT
<213> ORGANISM: Mus musculus

<400> SEQUENCE: 39

His Ile Trp Trp Asp Asp Asp Lys Tyr Tyr Ser Pro Ser Leu Lys Ser
1               5                   10                  15

<210> SEQ ID NO 40
<211> LENGTH: 16
<212> TYPE: PRT
<213> ORGANISM: Mus musculus

<400> SEQUENCE: 40

Ser Ile Ser Thr Gly Asp Arg Ser Tyr Leu Pro Asp Ser Met Lys Gly
1               5                   10                  15
```

<210> SEQ ID NO 41
<211> LENGTH: 16
<212> TYPE: PRT
<213> ORGANISM: Mus musculus

<400> SEQUENCE: 41

Tyr Ile Ser Tyr Ser Gly Ser Thr Tyr Tyr Asn Pro Ser Leu Arg Gly
1               5                   10                  15

<210> SEQ ID NO 42
<211> LENGTH: 16
<212> TYPE: PRT
<213> ORGANISM: Mus musculus

<400> SEQUENCE: 42

Phe Ile Ser Tyr Ser Gly Asn Thr Tyr Tyr Asn Pro Ser Leu Arg Ser
1               5                   10                  15

<210> SEQ ID NO 43
<211> LENGTH: 16
<212> TYPE: PRT
<213> ORGANISM: Rattus norvegicus

<400> SEQUENCE: 43

Asn Ile Trp Trp Asp Asp Asp Asn Tyr Tyr Asn Pro Ser Leu Ile His
1               5                   10                  15

<210> SEQ ID NO 44
<211> LENGTH: 16
<212> TYPE: PRT
<213> ORGANISM: Rattus norvegicus

<400> SEQUENCE: 44

Asn Ile Trp Trp Asp Asp Asp Lys Tyr Tyr Asn Pro Ser Leu Lys Asn
1               5                   10                  15

<210> SEQ ID NO 45
<211> LENGTH: 10
<212> TYPE: PRT
<213> ORGANISM: Mus musculus

<400> SEQUENCE: 45

Val Gly Gly Tyr Tyr Asp Ser Met Asp Tyr
1               5                   10

<210> SEQ ID NO 46
<211> LENGTH: 14
<212> TYPE: PRT
<213> ORGANISM: Rattus norvegicus

<400> SEQUENCE: 46

Gly Ser Phe Met Tyr Ala Ala Asp Tyr Tyr Ile Met Asp Ala
1               5                   10

<210> SEQ ID NO 47
<211> LENGTH: 9
<212> TYPE: PRT
<213> ORGANISM: Mus musculus

<400> SEQUENCE: 47

Gln Leu Gly Leu Arg Phe Phe Asp Tyr
1               5

<210> SEQ ID NO 48

```
<211> LENGTH: 9
<212> TYPE: PRT
<213> ORGANISM: Mus musculus

<400> SEQUENCE: 48

Lys Val Tyr Tyr Tyr Ala Met Asp Phe
1               5

<210> SEQ ID NO 49
<211> LENGTH: 10
<212> TYPE: PRT
<213> ORGANISM: Mus musculus

<400> SEQUENCE: 49

Leu Gly Gly Tyr Tyr Asp Thr Met Asp Tyr
1               5                   10

<210> SEQ ID NO 50
<211> LENGTH: 23
<212> TYPE: PRT
<213> ORGANISM: Mus musculus

<400> SEQUENCE: 50

Ser Tyr Tyr Tyr Gly Ser Ser Gly Ala Met Asp Tyr Trp Gly Gln Gly
1               5                   10                  15

Thr Ser Val Thr Val Ser Ser
            20

<210> SEQ ID NO 51
<211> LENGTH: 20
<212> TYPE: PRT
<213> ORGANISM: Mus musculus

<400> SEQUENCE: 51

Tyr Phe Asp Phe Asp Ser Phe Ala Phe Trp Gly Gln Gly Thr Leu Val
1               5                   10                  15

Thr Val Ser Ala
            20

<210> SEQ ID NO 52
<211> LENGTH: 23
<212> TYPE: PRT
<213> ORGANISM: Mus musculus

<400> SEQUENCE: 52

Arg His Leu Gly Ser Gly Tyr Gly Trp Phe Ala Tyr Trp Gly Gln Gly
1               5                   10                  15

Thr Leu Val Thr Val Ser Ala
            20

<210> SEQ ID NO 53
<211> LENGTH: 23
<212> TYPE: PRT
<213> ORGANISM: Mus musculus

<400> SEQUENCE: 53

Arg His Leu Ile Ser Gly Tyr Gly Trp Phe Ala Tyr Trp Gly Gln Gly
1               5                   10                  15

Thr Leu Val Thr Val Ser Ala
            20

<210> SEQ ID NO 54
<211> LENGTH: 22
<212> TYPE: PRT
```

<213> ORGANISM: Rattus norvegicus

<400> SEQUENCE: 54

Ile Lys Glu Pro Arg Asp Trp Phe Phe Glu Phe Trp Gly Pro Gly Thr
1               5                   10                  15

Met Val Ser Val Ser Ser
            20

<210> SEQ ID NO 55
<211> LENGTH: 22
<212> TYPE: PRT
<213> ORGANISM: Rattus norvegicus

<400> SEQUENCE: 55

Ile Lys Glu Pro Arg Asp Trp Phe Phe Glu Phe Trp Gly Pro Gly Thr
1               5                   10                  15

Met Val Ser Val Ser Ser
            20

<210> SEQ ID NO 56
<211> LENGTH: 15
<212> TYPE: PRT
<213> ORGANISM: Mus musculus

<400> SEQUENCE: 56

Arg Ala Ser Glu Ser Val Asp Asn Tyr Gly Val Ser Phe Met Asn
1               5                   10                  15

<210> SEQ ID NO 57
<211> LENGTH: 16
<212> TYPE: PRT
<213> ORGANISM: Rattus norvegicus

<400> SEQUENCE: 57

Arg Ser Ser Gln Ser Leu Leu His Ser Asp Gly Asn Thr Phe Leu Ser
1               5                   10                  15

<210> SEQ ID NO 58
<211> LENGTH: 10
<212> TYPE: PRT
<213> ORGANISM: Mus musculus

<400> SEQUENCE: 58

Ser Ala Asn Ser Thr Val Asn Tyr Met Tyr
1               5                   10

<210> SEQ ID NO 59
<211> LENGTH: 12
<212> TYPE: PRT
<213> ORGANISM: Mus musculus

<400> SEQUENCE: 59

Thr Ala Ser Ser Ser Val Ser Ser Ser Tyr Phe His
1               5                   10

<210> SEQ ID NO 60
<211> LENGTH: 15
<212> TYPE: PRT
<213> ORGANISM: Mus musculus

<400> SEQUENCE: 60

Arg Ala Ser Glu Ser Val Asp Asn Tyr Gly Ile Ser Phe Met Asn
1               5                   10                  15

<210> SEQ ID NO 61
<211> LENGTH: 16
<212> TYPE: PRT
<213> ORGANISM: Mus musculus

<400> SEQUENCE: 61

Arg Ser Ser Gln Ser Leu Val His Ser Asp Gly Asn Thr Tyr Leu His
1               5                   10                  15

<210> SEQ ID NO 62
<211> LENGTH: 11
<212> TYPE: PRT
<213> ORGANISM: Mus musculus

<400> SEQUENCE: 62

Arg Ala Ser Gln Asp Ile Asn Asn Phe Leu Asn
1               5                   10

<210> SEQ ID NO 63
<211> LENGTH: 11
<212> TYPE: PRT
<213> ORGANISM: Mus musculus

<400> SEQUENCE: 63

Lys Ala Ser Gln Asp Val Asn Thr Ala Val Ala
1               5                   10

<210> SEQ ID NO 64
<211> LENGTH: 11
<212> TYPE: PRT
<213> ORGANISM: Mus musculus

<400> SEQUENCE: 64

Lys Ala Ser Gln Asp Val Ile Ser Ala Val Ala
1               5                   10

<210> SEQ ID NO 65
<211> LENGTH: 11
<212> TYPE: PRT
<213> ORGANISM: Rattus norvegicus

<400> SEQUENCE: 65

Arg Ala Ser Gln Gly Val Asn Asn Phe Leu Thr
1               5                   10

<210> SEQ ID NO 66
<211> LENGTH: 11
<212> TYPE: PRT
<213> ORGANISM: Rattus norvegicus

<400> SEQUENCE: 66

Arg Ala Ser Gln Gly Val Asn Asn Tyr Leu Thr
1               5                   10

<210> SEQ ID NO 67
<211> LENGTH: 7
<212> TYPE: PRT
<213> ORGANISM: Mus musculus

<400> SEQUENCE: 67

Ala Ala Ser Asn Gln Gly Ser
1               5

<210> SEQ ID NO 68
<211> LENGTH: 7
<212> TYPE: PRT

<213> ORGANISM: Rattus norvegicus

<400> SEQUENCE: 68

Leu Ala Ser Asn Arg Phe Ser
1               5

<210> SEQ ID NO 69
<211> LENGTH: 7
<212> TYPE: PRT
<213> ORGANISM: Mus musculus

<400> SEQUENCE: 69

Leu Thr Ser Asn Leu Ala Ser
1               5

<210> SEQ ID NO 70
<211> LENGTH: 7
<212> TYPE: PRT
<213> ORGANISM: Mus musculus

<400> SEQUENCE: 70

Ser Thr Ser Asn Leu Ala Ser
1               5

<210> SEQ ID NO 71
<211> LENGTH: 7
<212> TYPE: PRT
<213> ORGANISM: Mus musculus

<400> SEQUENCE: 71

Ala Ala Ser Asn Gln Gly Ser
1               5

<210> SEQ ID NO 72
<211> LENGTH: 7
<212> TYPE: PRT
<213> ORGANISM: Mus musculus

<400> SEQUENCE: 72

Lys Val Ser Lys Arg Phe Ser
1               5

<210> SEQ ID NO 73
<211> LENGTH: 7
<212> TYPE: PRT
<213> ORGANISM: Mus musculus

<400> SEQUENCE: 73

Tyr Thr Ser Lys Leu His Ser
1               5

<210> SEQ ID NO 74
<211> LENGTH: 7
<212> TYPE: PRT
<213> ORGANISM: Mus musculus

<400> SEQUENCE: 74

Trp Ala Ser Thr Arg His Thr
1               5

<210> SEQ ID NO 75
<211> LENGTH: 7
<212> TYPE: PRT
<213> ORGANISM: Mus musculus

<400> SEQUENCE: 75

Trp Ala Ser Thr Arg His Thr
1               5

<210> SEQ ID NO 76
<211> LENGTH: 7
<212> TYPE: PRT
<213> ORGANISM: Rattus norvegicus

<400> SEQUENCE: 76

Tyr Thr Ser Asn Leu Gln Ser
1               5

<210> SEQ ID NO 77
<211> LENGTH: 7
<212> TYPE: PRT
<213> ORGANISM: Rattus norvegicus

<400> SEQUENCE: 77

Tyr Thr Ser Asn Leu Gln Ser
1               5

<210> SEQ ID NO 78
<211> LENGTH: 9
<212> TYPE: PRT
<213> ORGANISM: Mus musculus

<400> SEQUENCE: 78

Gln Gln Thr Lys Glu Val Thr Trp Thr
1               5

<210> SEQ ID NO 79
<211> LENGTH: 9
<212> TYPE: PRT
<213> ORGANISM: Rattus norvegicus

<400> SEQUENCE: 79

Phe Gln His Thr His Leu Pro Leu Thr
1               5

<210> SEQ ID NO 80
<211> LENGTH: 9
<212> TYPE: PRT
<213> ORGANISM: Mus musculus

<400> SEQUENCE: 80

Gln Gln Trp Asn Ser Asn Pro Pro Thr
1               5

<210> SEQ ID NO 81
<211> LENGTH: 9
<212> TYPE: PRT
<213> ORGANISM: Mus musculus

<400> SEQUENCE: 81

His Gln Tyr His Arg Ser Pro Arg Thr
1               5

<210> SEQ ID NO 82
<211> LENGTH: 9
<212> TYPE: PRT
<213> ORGANISM: Mus musculus

<400> SEQUENCE: 82

Gln Gln Ser Lys Glu Val Pro Phe Thr
1               5

```
<210> SEQ ID NO 83
<211> LENGTH: 9
<212> TYPE: PRT
<213> ORGANISM: Mus musculus

<400> SEQUENCE: 83

Ser Gln Ser Thr His Val Pro Pro Thr
1               5

<210> SEQ ID NO 84
<211> LENGTH: 9
<212> TYPE: PRT
<213> ORGANISM: Mus musculus

<400> SEQUENCE: 84

Gln Gln Gly His Thr Leu Pro Pro Thr
1               5

<210> SEQ ID NO 85
<211> LENGTH: 10
<212> TYPE: PRT
<213> ORGANISM: Mus musculus

<400> SEQUENCE: 85

Gln Gln His Ser Tyr Thr Pro Pro Trp Thr
1               5                   10

<210> SEQ ID NO 86
<211> LENGTH: 10
<212> TYPE: PRT
<213> ORGANISM: Mus musculus

<400> SEQUENCE: 86

Gln Gln His Ser Tyr Thr Pro Pro Trp Thr
1               5                   10

<210> SEQ ID NO 87
<211> LENGTH: 9
<212> TYPE: PRT
<213> ORGANISM: Rattus norvegicus

<400> SEQUENCE: 87

Gln Gln Tyr His Gly Phe Pro Asn Thr
1               5

<210> SEQ ID NO 88
<211> LENGTH: 9
<212> TYPE: PRT
<213> ORGANISM: Rattus norvegicus

<400> SEQUENCE: 88

Gln Gln Tyr His Gly Phe Pro Asn Thr
1               5

<210> SEQ ID NO 89
<211> LENGTH: 241
<212> TYPE: PRT
<213> ORGANISM: Homo sapiens
<220> FEATURE:
<221> NAME/KEY: SIGNAL
<222> LOCATION: (1)..(25)

<400> SEQUENCE: 89

Met Ala Gln His Gly Ala Met Gly Ala Phe Arg Ala Leu Cys Gly Leu
1               5                   10                  15
```

Ala Leu Leu Cys Ala Leu Ser Leu Gly Gln Arg Pro Thr Gly Gly Pro
             20                  25                  30

Gly Cys Gly Pro Gly Arg Leu Leu Leu Gly Thr Gly Thr Asp Ala Arg
         35                  40                  45

Cys Cys Arg Val His Thr Thr Arg Cys Cys Arg Asp Tyr Pro Gly Glu
 50                  55                  60

Glu Cys Cys Ser Glu Trp Asp Cys Met Cys Val Gln Pro Glu Phe His
 65                  70                  75                  80

Cys Gly Asp Pro Cys Cys Thr Thr Cys Arg His His Pro Cys Pro Pro
                 85                  90                  95

Gly Gln Gly Val Gln Ser Gln Gly Lys Phe Ser Phe Gly Phe Gln Cys
             100                 105                 110

Ile Asp Cys Ala Ser Gly Thr Phe Ser Gly Gly His Glu Gly His Cys
             115                 120                 125

Lys Pro Trp Thr Asp Cys Thr Gln Phe Gly Phe Leu Thr Val Phe Pro
130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Ser Gln Cys Met Trp Pro Arg Glu Thr Gln Leu Leu Leu Glu Val
            195                 200                 205

Pro Pro Ser Thr Glu Asp Ala Arg Ser Cys Gln Phe Pro Glu Glu Glu
        210                 215                 220

Arg Gly Glu Arg Ser Ala Glu Glu Lys Gly Arg Leu Gly Asp Leu Trp
225                 230                 235                 240

Val

<210> SEQ ID NO 90
<211> LENGTH: 122
<212> TYPE: PRT
<213> ORGANISM: Artificial Sequence
<220> FEATURE:
<223> OTHER INFORMATION: humanized antibody sequence
<220> FEATURE:
<221> NAME/KEY: VARIANT
<222> LOCATION: (24)..(24)
<223> OTHER INFORMATION: Can be A or F
<220> FEATURE:
<221> NAME/KEY: VARIANT
<222> LOCATION: (69)..(69)
<223> OTHER INFORMATION: Can be F or L
<220> FEATURE:
<221> NAME/KEY: VARIANT
<222> LOCATION: (73)..(73)
<223> OTHER INFORMATION: Can be R or K
<220> FEATURE:
<221> NAME/KEY: VARIANT
<222> LOCATION: (75)..(75)
<223> OTHER INFORMATION: Can be N or T
<220> FEATURE:
<221> NAME/KEY: VARIANT
<222> LOCATION: (80)..(80)
<223> OTHER INFORMATION: Can be L or V
<220> FEATURE:
<221> NAME/KEY: VARIANT
<222> LOCATION: (98)..(98)
<223> OTHER INFORMATION: Can be A or V

<400> SEQUENCE: 90

Gln Val Gln Leu Val Glu Ser Gly Gly Gly Val Val Gln Pro Gly Arg

```
                        1               5                  10                 15
Ser Leu Arg Leu Ser Cys Ala Xaa Ser Gly Phe Ser Leu Ser Thr Ser
                    20                  25                 30

Gly Met Gly Val Gly Trp Val Arg Gln Ala Pro Gly Lys Gly Leu Glu
            35                  40                  45

Trp Val Ala His Ile Trp Trp Asp Asp Lys Tyr Tyr Ser Pro Ser
    50                  55                  60

Leu Lys Ser Arg Xaa Thr Ile Ser Xaa Asp Xaa Ser Lys Asn Thr Xaa
65                  70                  75                  80

Tyr Leu Gln Met Asn Ser Leu Arg Ala Glu Asp Thr Ala Val Tyr Tyr
                85                  90                  95

Cys Xaa Arg Ser Tyr Tyr Tyr Gly Ser Ser Gly Ala Met Asp Tyr Trp
                100                 105                 110

Gly Gln Gly Thr Leu Val Thr Val Ser Ser
            115                 120
```

<210> SEQ ID NO 91
<211> LENGTH: 113
<212> TYPE: PRT
<213> ORGANISM: Artificial Sequence
<220> FEATURE:
<223> OTHER INFORMATION: Humanized antibody sequence

<400> SEQUENCE: 91

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asp Gly Asn Thr Tyr Leu His Trp Tyr Leu Gln Lys Pro Gly Gln Ser
            35                  40                  45

Pro Gln Leu Leu Ile Tyr Lys Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Thr Phe Gly Gln Gly Thr Lys Val Glu Ile Lys
            100                 105                 110

Arg
```

<210> SEQ ID NO 92
<211> LENGTH: 123
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (97)..(97)
<223> OTHER INFORMATION: Can be A or T
<220> FEATURE:
<221> NAME/KEY: VARIANT
<222> LOCATION: (98)..(98)
<223> OTHER INFORMATION: Can be R or T

<400> SEQUENCE: 92

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
                20                  25                  30
```

```
Tyr Met Ala Trp Val Arg Gln Ala Pro Gly Lys Gly Leu Glu Trp Val
         35                  40                  45

Ala Tyr Ile His Ala Asn Gly Gly Ser Thr Tyr Tyr Arg Asp Ser Val
     50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Xaa Xaa Gly Ser Phe Met Tyr Ala Ala Asp Tyr Tyr Ile Met Asp Ala
             100                 105                 110

Trp Gly Gln Gly Thr Leu Val Thr Val Ser Ser
        115                 120
```

<210> SEQ ID NO 93
<211> LENGTH: 113
<212> TYPE: PRT
<213> ORGANISM: Artificial Sequence
<220> FEATURE:
<223> OTHER INFORMATION: Humanized antibody sequence

<400> SEQUENCE: 93

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

Asp Gly Asn Thr Phe Leu Ser Trp Tyr Leu Gln Lys Pro Gly Gln Ser
         35                  40                  45

Pro Gln Leu Leu Ile Tyr Leu Ala Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln His
                 85                  90                  95

Thr His Leu Pro Leu Thr Phe Gly Gln Gly Thr Lys Val Glu Ile Lys
             100                 105                 110

Arg
```

<210> SEQ ID NO 94
<211> LENGTH: 118
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (48)..(48)
<223> OTHER INFORMATION: Can be M or I
<220> FEATURE:
<221> NAME/KEY: VARIANT
<222> LOCATION: (68)..(68)
<223> OTHER INFORMATION: Can be V or A
<220> FEATURE:
<221> NAME/KEY: VARIANT
<222> LOCATION: (70)..(70)
<223> OTHER INFORMATION: Can be M or F
<220> FEATURE:
<221> NAME/KEY: VARIANT
<222> LOCATION: (72)..(72)
<223> OTHER INFORMATION: Can be T or A

<400> SEQUENCE: 94

```
Gln Val Gln Leu Val Gln Ser Gly Ala Glu Val Lys Lys Pro Gly Ala
 1               5                  10                  15
```

```
Ser Val Lys Val Ser Cys Lys Ala Ser Gly Tyr Thr Phe Ser Arg Tyr
            20                  25                  30

Trp Ile Glu Trp Val Arg Gln Ala Pro Gly Gln Gly Leu Glu Trp Xaa
        35                  40                  45

Gly Glu Ile Leu Pro Gly Ser Gly Ser Ser Asn Tyr Asn Glu Lys Phe
    50                  55                  60

Lys Asp Arg Xaa Thr Xaa Thr Xaa Asp Thr Ser Thr Ser Thr Ala Tyr
65              70                  75                  80

Met Glu Leu Arg Ser Leu Arg Ser Asp Asp Thr Ala Val Tyr Tyr Cys
                85                  90                  95

Ala Arg Lys Val Tyr Tyr Ala Met Asp Phe Trp Gly Gln Gly Thr
                100                 105                 110

Leu Val Thr Val Ser Ser
        115
```

```
<210> SEQ ID NO 95
<211> LENGTH: 109
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (48)..(48)
<223> OTHER INFORMATION: Can be L or W
<220> FEATURE:
<221> NAME/KEY: VARIANT
<222> LOCATION: (72)..(72)
<223> OTHER INFORMATION: Can be F or Y

<400> SEQUENCE: 95
```

```
Glu Ile Val Leu Thr Gln Ser Pro Gly Thr Leu Ser Leu Ser Pro Gly
1               5                   10                  15

Glu Arg Ala Thr Leu Ser Cys Thr Ala Ser Ser Ser Val Ser Ser Ser
            20                  25                  30

Tyr Phe His Trp Tyr Gln Gln Lys Pro Gly Gln Ala Pro Arg Leu Xaa
        35                  40                  45

Ile Tyr Ser Thr Ser Asn Leu Ala Ser Gly Ile Pro Asp Arg Phe Ser
    50                  55                  60

Gly Ser Gly Ser Gly Thr Asp Xaa Thr Leu Thr Ile Ser Arg Leu Glu
65              70                  75                  80

Pro Glu Asp Phe Ala Val Tyr Tyr Cys His Gln Tyr His Arg Ser Pro
                85                  90                  95

Arg Thr Phe Gly Gln Gly Thr Lys Val Glu Ile Lys Arg
                100                 105
```

```
<210> SEQ ID NO 96
<211> LENGTH: 121
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (24)..(24)
<223> OTHER INFORMATION: Can be V or F
<220> FEATURE:
<221> NAME/KEY: VARIANT
<222> LOCATION: (50)..(50)
<223> OTHER INFORMATION: Can be I or L
<220> FEATURE:
<221> NAME/KEY: VARIANT
<222> LOCATION: (51)..(51)
<223> OTHER INFORMATION: Can be G or A
<220> FEATURE:
```

```
<221> NAME/KEY: VARIANT
<222> LOCATION: (69)..(69)
<223> OTHER INFORMATION: Can be V or L
<220> FEATURE:
<221> NAME/KEY: VARIANT
<222> LOCATION: (71)..(71)
<223> OTHER INFORMATION: Can be I or V
<220> FEATURE:
<221> NAME/KEY: VARIANT
<222> LOCATION: (73)..(73)
<223> OTHER INFORMATION: Can be V or K
<220> FEATURE:
<221> NAME/KEY: VARIANT
<222> LOCATION: (80)..(80)
<223> OTHER INFORMATION: Can be F or A
<220> FEATURE:
<221> NAME/KEY: VARIANT
<222> LOCATION: (99)..(99)
<223> OTHER INFORMATION: Can be R or Q

<400> SEQUENCE: 96

Gln Val Gln Leu Gln Glu Ser Gly Pro Gly Leu Val Lys Pro Ser Glu
 1               5                  10                  15

Thr Leu Ser Leu Thr Cys Thr Xaa Ser Gly Phe Ser Leu Ser Thr Tyr
            20                  25                  30

Gly Val Gly Val Gly Trp Ile Arg Gln Pro Pro Gly Lys Gly Leu Glu
        35                  40                  45

Trp Xaa Xaa Asn Ile Trp Asp Asp Asp Asn Tyr Tyr Asn Pro Ser
    50                  55                  60

Leu Ile His Arg Xaa Thr Xaa Ser Xaa Asp Thr Ser Lys Asn Gln Xaa
65                  70                  75                  80

Ser Leu Lys Leu Ser Ser Val Thr Ala Ala Asp Thr Ala Val Tyr Tyr
                85                  90                  95

Cys Ala Xaa Ile Lys Glu Pro Arg Asp Trp Phe Phe Glu Phe Trp Gly
            100                 105                 110

Gln Gly Thr Leu Val Thr Val Ser Ser
        115                 120

<210> SEQ ID NO 97
<211> LENGTH: 108
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (46)..(46)
<223> OTHER INFORMATION: Can be L or P
<220> FEATURE:
<221> NAME/KEY: VARIANT
<222> LOCATION: (49)..(49)
<223> OTHER INFORMATION: Can be Y or F
<220> FEATURE:
<221> NAME/KEY: VARIANT
<222> LOCATION: (71)..(71)
<223> OTHER INFORMATION: Can be F or Y

<400> SEQUENCE: 97

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Val Asn Asn Phe
            20                  25                  30

Leu Thr Trp Tyr Gln Gln Lys Pro Gly Lys Ala Pro Lys Xaa Leu Ile
        35                  40                  45

Xaa Tyr Thr Ser Asn Leu Gln Ser Gly Val Pro Ser Arg Phe Ser Gly
    50                  55                  60
```

```
Ser Gly Ser Gly Thr Asp Xaa Thr Leu Thr Ile Ser Ser Leu Gln Pro
 65                  70                  75                  80

Glu Asp Phe Ala Thr Tyr Tyr Cys Gln Gln Tyr His Gly Phe Pro Asn
                 85                  90                  95

Thr Phe Gly Gln Gly Thr Lys Val Glu Ile Lys Arg
            100                 105
```

<210> SEQ ID NO 98
<211> LENGTH: 121
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (24)..(24)
<223> OTHER INFORMATION: Can be V or F
<220> FEATURE:
<221> NAME/KEY: VARIANT
<222> LOCATION: (50)..(50)
<223> OTHER INFORMATION: Can be I or L
<220> FEATURE:
<221> NAME/KEY: VARIANT
<222> LOCATION: (51)..(51)
<223> OTHER INFORMATION: Can be G or A
<220> FEATURE:
<221> NAME/KEY: VARIANT
<222> LOCATION: (69)..(69)
<223> OTHER INFORMATION: Can be V or L
<220> FEATURE:
<221> NAME/KEY: VARIANT
<222> LOCATION: (73)..(73)
<223> OTHER INFORMATION: Can be V or K
<220> FEATURE:
<221> NAME/KEY: VARIANT
<222> LOCATION: (80)..(80)
<223> OTHER INFORMATION: Can be F or A
<220> FEATURE:
<221> NAME/KEY: VARIANT
<222> LOCATION: (99)..(99)
<223> OTHER INFORMATION: Can be R or Q

<400> SEQUENCE: 98

```
Gln Val Gln Leu Gln Glu Ser Gly Pro Gly Leu Val Lys Pro Ser Glu
 1               5                   10                  15

Thr Leu Ser Leu Thr Cys Thr Xaa Ser Gly Phe Ser Leu Ser Thr Tyr
             20                  25                  30

Gly Val Gly Val Gly Trp Ile Arg Gln Pro Pro Gly Lys Gly Leu Glu
             35                  40                  45

Trp Xaa Xaa Asn Ile Trp Trp Asp Asp Lys Tyr Tyr Asn Pro Ser
 50                  55                  60

Leu Lys Asn Arg Xaa Thr Ile Ser Xaa Asp Thr Ser Lys Asn Gln Xaa
 65                  70                  75                  80

Ser Leu Lys Leu Ser Ser Val Thr Ala Ala Asp Thr Ala Val Tyr Tyr
             85                  90                  95

Cys Ala Xaa Ile Lys Glu Pro Arg Asp Trp Phe Phe Gly Phe Trp Gly
            100                 105                 110

Gln Gly Thr Leu Val Thr Val Ser Ser
        115                 120
```

<210> SEQ ID NO 99
<211> LENGTH: 108
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT

```
<222> LOCATION: (46)..(46)
<223> OTHER INFORMATION: Can be L or P
<220> FEATURE:
<221> NAME/KEY: VARIANT
<222> LOCATION: (49)..(49)
<223> OTHER INFORMATION: Can be Y or F
<220> FEATURE:
<221> NAME/KEY: VARIANT
<222> LOCATION: (71)..(71)
<223> OTHER INFORMATION: Can be F or Y

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Asn Asn Tyr
            20                  25                  30

Leu Thr Trp Tyr Gln Gln Lys Pro Gly Lys Ala Pro Lys Xaa Leu Ile
        35                  40                  45

Xaa Tyr Thr Ser Asn Leu Gln Ser Gly Val Pro Ser Arg Phe Ser Gly
50                  55                  60

Ser Gly Ser Gly Thr Asp Xaa Thr Leu Thr Ile Ser Ser Leu Gln Pro
65                  70                  75                  80

Glu Asp Phe Ala Thr Tyr Tyr Cys Gln Gln Tyr His Gly Phe Pro Asn
                85                  90                  95

Thr Phe Gly Gln Gly Thr Lys Val Glu Ile Lys Arg
            100                 105

<210> SEQ ID NO 100
<211> LENGTH: 117
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (96)..(96)
<223> OTHER INFORMATION: Can be A or Q

<400> SEQUENCE: 100

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Val Arg Asn Tyr
            20                  25                  30

Ala Met Ser Trp Val Arg Gln Ala Pro Gly Lys Gly Leu Glu Trp Val
        35                  40                  45

Ala Ser Ile Ser Thr Gly Asp Arg Ser Tyr Leu Pro Asp Ser Met Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Xaa
                85                  90                  95

Arg Tyr Phe Asp Phe Asp Ser Phe Ala Phe Trp Gly Gln Gly Thr Leu
            100                 105                 110

Val Thr Val Ser Ser
        115

<210> SEQ ID NO 101
<211> LENGTH: 108
<212> TYPE: PRT
<213> ORGANISM: Artificial Sequence
<220> FEATURE:
<223> OTHER INFORMATION: Humanized antibody sequence
```

```
<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Phe
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys Arg
            100                 105
```

```
<210> SEQ ID NO 102
<211> LENGTH: 120
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (47)..(47)
<223> OTHER INFORMATION: Can be W or Y
<220> FEATURE:
<221> NAME/KEY: VARIANT
<222> LOCATION: (48)..(48)
<223> OTHER INFORMATION: Can be I or M
<220> FEATURE:
<221> NAME/KEY: VARIANT
<222> LOCATION: (71)..(71)
<223> OTHER INFORMATION: Can be V or R
<220> FEATURE:
<221> NAME/KEY: VARIANT
<222> LOCATION: (96)..(96)
<223> OTHER INFORMATION: Can be A or S

<400> SEQUENCE: 102

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln Pro Pro Gly Lys Gly Leu Glu Xaa Xaa
        35                  40                  45

Gly Tyr Ile Ser Tyr Ser Gly Ser Thr Tyr Tyr Asn Pro Ser Leu Arg
    50                  55                  60

Gly Arg Val Thr Ile Ser Xaa Asp Thr Ser Lys Asn Gln Phe Ser Leu
65                  70                  75                  80

Lys Leu Ser Ser Val Thr Ala Ala Asp Thr Ala Val Tyr Tyr Cys Xaa
                85                  90                  95

Arg Arg His Leu Gly Ser Gly Tyr Gly Trp Phe Ala Tyr Trp Gly Gln
            100                 105                 110

Gly Thr Leu Val Thr Val Ser Ser
            115                 120
```

```
<210> SEQ ID NO 103
<211> LENGTH: 109
<212> TYPE: PRT
<213> ORGANISM: Artificial Sequence
<220> FEATURE:
<223> OTHER INFORMATION: Humanized antibody sequence
```

```
<220> FEATURE:
<221> NAME/KEY: VARIANT
<222> LOCATION: (71)..(71)
<223> OTHER INFORMATION: Can be F or Y

<400> SEQUENCE: 103

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Asn Thr Ala
            20                  25                  30

Val Ala Trp Tyr Gln Gln Lys Pro Gly Gln Pro Pro Lys Leu Leu Ile
        35                  40                  45

Tyr Trp Ala Ser Thr Arg His Thr Gly Val Pro Asp Arg Phe Ser Gly
50                  55                  60

Ser Gly Ser Gly Thr Asp Xaa Thr Leu Thr Ile Ser Ser Leu Gln Ala
65                  70                  75                  80

Glu Asp Val Ala Val Tyr Tyr Cys Gln Gln His Ser Tyr Thr Pro Pro
                85                  90                  95

Trp Thr Phe Gly Gln Gly Thr Lys Val Glu Ile Lys Arg
            100                 105

<210> SEQ ID NO 104
<211> LENGTH: 118
<212> TYPE: PRT
<213> ORGANISM: Artificial Sequence
<220> FEATURE:
<223> OTHER INFORMATION: Humanized antibody sequence

<400> SEQUENCE: 104

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Thr Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Val Gly Gly Tyr Tyr Asp Ser Met Asp Tyr Trp Gly Gln Gly Thr
            100                 105                 110

Leu Val Thr Val Ser Ser
        115

<210> SEQ ID NO 105
<211> LENGTH: 112
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (31)..(31)
<223> OTHER INFORMATION: Can be N or Q
<220> FEATURE:
<221> NAME/KEY: VARIANT
<222> LOCATION: (57)..(57)
<223> OTHER INFORMATION: Can be N or Q

<400> SEQUENCE: 105
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Glu Ser Val Asp Xaa Tyr
            20                  25                  30

Gly Val Ser Phe Met Asn Trp Tyr Gln Gln Lys Pro Gly Gln Ala Pro
        35                  40                  45

Arg Leu Leu Ile Tyr Ala Ala Ser Xaa Gln Gly Ser Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Thr Lys
                85                  90                  95

Glu Val Thr Trp Thr Phe Gly Gln Gly Thr Lys Val Glu Ile Lys Arg
            100                 105                 110
```

<210> SEQ ID NO 106
<211> LENGTH: 120
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (47)..(47)
<223> OTHER INFORMATION: Can be W or Y
<220> FEATURE:
<221> NAME/KEY: VARIANT
<222> LOCATION: (48)..(48)
<223> OTHER INFORMATION: Can be I or M
<220> FEATURE:
<221> NAME/KEY: VARIANT
<222> LOCATION: (67)..(67)
<223> OTHER INFORMATION: Can be V or I
<220> FEATURE:
<221> NAME/KEY: VARIANT
<222> LOCATION: (71)..(71)
<223> OTHER INFORMATION: Can be V or R
<220> FEATURE:
<221> NAME/KEY: VARIANT
<222> LOCATION: (78)..(78)
<223> OTHER INFORMATION: Can be F or Y
<220> FEATURE:
<221> NAME/KEY: VARIANT
<222> LOCATION: (96)..(96)
<223> OTHER INFORMATION: Can be A or S

<400> SEQUENCE: 106

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln Pro Pro Gly Lys Gly Leu Glu Xaa Xaa
        35                  40                  45

Gly Phe Ile Ser Tyr Ser Gly Asn Thr Tyr Tyr Asn Pro Ser Leu Arg
    50                  55                  60

Ser Arg Xaa Thr Ile Ser Xaa Asp Thr Ser Lys Asn Gln Xaa Ser Leu
65                  70                  75                  80

Lys Leu Ser Ser Val Thr Ala Ala Asp Thr Ala Val Tyr Tyr Cys Xaa
                85                  90                  95

Arg Arg His Leu Ile Ser Gly Tyr Gly Trp Phe Ala Tyr Trp Gly Gln
            100                 105                 110

Gly Thr Leu Val Thr Val Ser Ser
            115                 120
```

<210> SEQ ID NO 107
<211> LENGTH: 109
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (1)..(1)
<223> OTHER INFORMATION: Can be D or V

<400> SEQUENCE: 107

Xaa Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ile Ser Ala
            20                  25                  30

Val Ala Trp Tyr Gln Gln Lys Pro Gly Gln Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His Ser Tyr Thr Pro Pro
                85                  90                  95

Trp Thr Phe Gly Gln Gly Thr Lys Val Glu Ile Lys Arg
            100                 105

<210> SEQ ID NO 108
<211> LENGTH: 119
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (48)..(48)
<223> OTHER INFORMATION: Can be M or I
<220> FEATURE:
<221> NAME/KEY: VARIANT
<222> LOCATION: (68)..(68)
<223> OTHER INFORMATION: Can be V or A
<220> FEATURE:
<221> NAME/KEY: VARIANT
<222> LOCATION: (70)..(70)
<223> OTHER INFORMATION: Can be M or L
<220> FEATURE:
<221> NAME/KEY: VARIANT
<222> LOCATION: (72)..(72)
<223> OTHER INFORMATION: Can be T or A
<220> FEATURE:
<221> NAME/KEY: VARIANT
<222> LOCATION: (74)..(74)
<223> OTHER INFORMATION: Can be T or K

<400> SEQUENCE: 108

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Xaa
        35                  40                  45

Gly Tyr Ile Asn Pro Arg Ser Val Tyr Thr Asn Tyr Asn Gln Lys Phe
    50                  55                  60

Lys Asp Arg Xaa Thr Xaa Thr Xaa Asp Xaa Ser Thr Ser Thr Ala Tyr
65                  70                  75                  80

Met Glu Leu Arg Ser Leu Arg Ser Asp Asp Thr Ala Val Tyr Tyr Cys

```
                  85                  90                  95

Ala Arg Leu Gly Gly Tyr Tyr Asp Thr Met Asp Tyr Trp Gly Gln Gly
            100                 105                 110

Thr Leu Val Thr Val Ser Ser
        115

<210> SEQ ID NO 109
<211> LENGTH: 112
<212> TYPE: PRT
<213> ORGANISM: Artificial Sequence
<220> FEATURE:
<223> OTHER INFORMATION: Humanized antibody sequence

<400> SEQUENCE: 109

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Tyr Gln Gln Lys Pro Gly Lys Ala Pro
        35                  40                  45

Lys Leu Leu Ile Tyr Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Lys
                85                  90                  95

Glu Val Pro Phe Thr Phe Gly Gln Gly Thr Lys Val Glu Ile Lys Arg
            100                 105                 110

<210> SEQ ID NO 110
<211> LENGTH: 118
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (49)..(49)
<223> OTHER INFORMATION: Can be I or M
<220> FEATURE:
<221> NAME/KEY: VARIANT
<222> LOCATION: (68)..(68)
<223> OTHER INFORMATION: Can be V or I
<220> FEATURE:
<221> NAME/KEY: VARIANT
<222> LOCATION: (72)..(72)
<223> OTHER INFORMATION: Can be V or R

<400> SEQUENCE: 110

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Xaa Gly Tyr Ile Ser Tyr Ser Gly Ser Thr Arg Tyr Asn Pro Ser Leu
    50                  55                  60

Lys Ser Arg Xaa Thr Ile Ser Xaa Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gln Leu Gly Leu Arg Phe Phe Asp Tyr Trp Gly Gln Gly Thr
```

```
                    100                 105                 110
Leu Val Thr Val Ser Ser
            115

<210> SEQ ID NO 111
<211> LENGTH: 107
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (45)..(45)
<223> OTHER INFORMATION: Can be L or P
<220> FEATURE:
<221> NAME/KEY: VARIANT
<222> LOCATION: (46)..(46)
<223> OTHER INFORMATION: Can be L or C

<400> SEQUENCE: 111

Glu Ile Val Leu Thr Gln Ser Pro Gly Thr Leu Ser Leu Ser Pro Gly
1               5                   10                  15

Glu Arg Ala Thr Leu Ser Cys Ser Ala Asn Ser Thr Val Asn Tyr Met
            20                  25                  30

Tyr Trp Tyr Gln Gln Lys Pro Gly Gln Ala Pro Arg Xaa Xaa Ile Tyr
        35                  40                  45

Leu Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Asn Ser Asn Pro Pro Thr
                85                  90                  95

Phe Gly Gln Gly Thr Lys Val Glu Ile Lys Arg
                100                 105
```